(12) United States Patent
Bonadio et al.

(10) Patent No.: US 7,300,399 B2
(45) Date of Patent: *Nov. 27, 2007

(54) SURGICAL DEVICE FOR RETRACTING AND/OR SEALING AN INCISION

(75) Inventors: Frank Bonadio, Bray (IE); Shane Joseph McNally, Dublin (IE); Ronan Bernard McManus, Bray (IE); Derek William Young, County Dublin (IE); Alan Reid, Dublin (IE)

(73) Assignee: Atropos Limited, County Wicklow (IE)

( * ) Notice: Subject to any disclaimer, the term of this patent is extended or adjusted under 35 U.S.C. 154(b) by 0 days.

This patent is subject to a terminal disclaimer.

(21) Appl. No.: 10/995,117

(22) Filed: Nov. 24, 2004

(65) Prior Publication Data

US 2005/0090716 A1  Apr. 28, 2005

Related U.S. Application Data

(63) Continuation of application No. 10/133,979, filed on Apr. 29, 2002, now Pat. No. 6,846,287, which is a continuation of application No. 09/801,826, filed on Mar. 9, 2001, now abandoned, which is a continuation of application No. PCT/IE99/00122, filed on Dec. 1, 1999.

(30) Foreign Application Priority Data

| | | | |
|---|---|---|---|
| Dec. 1, 1998 | (IE) | | 980997 |
| Feb. 15, 1999 | (IE) | | 990111 |

(51) Int. Cl.
*A61B 1/32* (2006.01)

(52) U.S. Cl. .................................................. 600/208

(58) Field of Classification Search ................ 600/201, 600/206, 207, 208, 235; 606/213, 215, 216; 128/846, 849, 850, 888
See application file for complete search history.

(56) References Cited

U.S. PATENT DOCUMENTS

| | | | |
|---|---|---|---|
| 1,157,202 A | 10/1915 | McLeland |
| 1,598,284 A | 8/1926 | Kinney |
| 1,810,466 A | 6/1931 | Deutsch |
| 2,219,564 A | 10/1940 | Reyniers |
| 2,305,289 A | 12/1942 | Coburg |
| 2,695,608 A | 11/1954 | Gibbon |
| 2,835,253 A | 5/1958 | Borgeson |
| 2,853,075 A | 10/1958 | Hoffman |
| 3,039,468 A | 6/1962 | Price |
| 3,111,943 A | 11/1963 | Orndorff |
| 3,244,169 A | 4/1966 | Baxter |

(Continued)

FOREIGN PATENT DOCUMENTS

DE     37 39 532     12/1988

(Continued)

*Primary Examiner*—Anuradha Ramana
(74) *Attorney, Agent, or Firm*—Finnegan, Henderson, Farabow, Garrett & Dunner, LLP

(57) ABSTRACT

A wound protector retractor comprises an inner O-ring for insertion through a wound opening and a connecting sleeve extending between the O-ring and outer mounting means. The outer means are provided by rings between which the sleeve is led. The rings are rotated relative to each other and the inner ring to form a centralised lumen of reduced cross section and to shorten the axial extent of the sleeve. A wound is both retracted and protected.

38 Claims, 16 Drawing Sheets

U.S. PATENT DOCUMENTS

| | | |
|---|---|---|
| 3,253,594 A | 5/1966 | Matthews et al. |
| 3,313,299 A | 4/1967 | Spademan |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,656,485 A | 4/1972 | Robertson |
| 3,685,786 A | 8/1972 | Woodson |
| 3,717,151 A | 2/1973 | Collett |
| 3,729,006 A | 4/1973 | Wilder et al. |
| 3,782,370 A | 1/1974 | McDonald |
| 3,797,478 A | 3/1974 | Walsh et al. |
| 3,807,393 A | 4/1974 | McDonald |
| 3,828,764 A | 8/1974 | Jones |
| 3,841,332 A | 10/1974 | Treacle |
| 3,853,126 A | 12/1974 | Schulte |
| 3,853,127 A | 12/1974 | Spademan |
| 3,856,021 A | 12/1974 | Macintosh |
| 3,907,389 A | 9/1975 | Cox et al. |
| 3,915,171 A | 10/1975 | Shermeta |
| 3,965,890 A | 6/1976 | Gauthier |
| 3,996,623 A | 12/1976 | Kaster |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,083,370 A | 4/1978 | Taylor |
| 4,096,853 A | 6/1978 | Weigand |
| 4,130,113 A | 12/1978 | Graham |
| 4,177,814 A | 12/1979 | Knepshield |
| 4,188,945 A | 2/1980 | Wenander |
| 4,217,664 A | 8/1980 | Faso |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lehrman |
| 4,367,728 A | 1/1983 | Mutke |
| 4,399,816 A | 8/1983 | Spangler |
| 4,411,659 A * | 10/1983 | Jensen et al. ............... 604/332 |
| 4,421,296 A | 12/1983 | Stephens |
| 4,424,833 A | 1/1984 | Spector |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,485,490 A | 12/1984 | Akers et al. |
| 4,488,877 A | 12/1984 | Klein |
| 4,543,088 A | 9/1985 | Bootman |
| 4,550,713 A | 11/1985 | Hyman |
| 4,553,537 A | 11/1985 | Rosenberg |
| 4,601,710 A | 7/1986 | Moll |
| 4,610,665 A | 9/1986 | Matsumoto |
| 4,626,245 A | 12/1986 | Weinstein |
| 4,634,424 A | 1/1987 | O'Boyle |
| 4,649,904 A | 3/1987 | Krauter |
| 4,654,030 A | 3/1987 | Moll et al. |
| 4,673,393 A | 6/1987 | Suzuki et al. |
| 4,673,394 A | 6/1987 | Fenton |
| 4,755,170 A | 7/1988 | Golden |
| 4,777,943 A | 10/1988 | Chvapil |
| 4,784,646 A | 11/1988 | Feingold |
| 4,798,594 A | 1/1989 | Hillstead |
| 4,809,679 A | 3/1989 | Shimonaka |
| 4,863,438 A | 9/1989 | Gauderer |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,015,228 A | 5/1991 | Columbus et al. |
| 5,019,101 A | 5/1991 | Purkait |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,074,878 A | 12/1991 | Bark et al. |
| 5,082,005 A | 1/1992 | Kaldany |
| 5,092,846 A | 3/1992 | Nishijima |
| 5,125,897 A | 6/1992 | Quinn et al. |
| 5,141,498 A | 8/1992 | Christian |
| 5,149,327 A | 9/1992 | Oshiyama |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,178,162 A | 1/1993 | Bose |
| 5,188,595 A | 2/1993 | Jacobi |
| 5,192,301 A | 3/1993 | Kamiya et al. |
| 5,207,656 A | 5/1993 | Kranys |
| 5,209,737 A | 5/1993 | Richartt |
| 5,211,370 A | 5/1993 | Powers |
| 5,211,633 A | 5/1993 | Stouder |
| 5,213,114 A | 5/1993 | Bailey, Jr. |
| 5,234,455 A | 8/1993 | Mulhollan |
| 5,242,409 A | 9/1993 | Buelna |
| 5,248,304 A | 9/1993 | Vigdorchik et al. |
| 5,263,922 A | 11/1993 | Sova et al. |
| 5,269,763 A | 12/1993 | Boehmer |
| D343,236 S | 1/1994 | Quigley et al. |
| 5,279,575 A | 1/1994 | Sugarbaker |
| D346,022 S | 4/1994 | Quigley et al. |
| 5,299,582 A | 4/1994 | Potts |
| 5,300,036 A | 4/1994 | Mueller |
| 5,308,336 A | 5/1994 | Hart et al. |
| 5,309,896 A | 5/1994 | Moll et al. |
| 5,316,541 A | 5/1994 | Fischer |
| 5,320,611 A | 6/1994 | Bonutti |
| 5,330,437 A | 7/1994 | Durman |
| 5,330,497 A | 7/1994 | Freitas |
| 5,336,192 A | 8/1994 | Palestrant |
| 5,342,385 A | 8/1994 | Norelli et al. |
| 5,350,364 A | 9/1994 | Stephens et al. |
| 5,364,345 A | 11/1994 | Lowery et al. |
| 5,366,478 A | 11/1994 | Brinkerhoff et al. |
| 5,368,545 A | 11/1994 | Schaller et al. |
| 5,383,861 A | 1/1995 | Hempel |
| 5,385,553 A | 1/1995 | Hart et al. |
| 5,391,156 A | 2/1995 | Hildwein et al. |
| 5,403,264 A | 4/1995 | Wohlers |
| 5,407,433 A | 4/1995 | Loomas |
| 5,429,609 A | 7/1995 | Yoon |
| 5,431,676 A | 7/1995 | Durbal |
| 5,443,452 A | 8/1995 | Hart et al. |
| 5,456,284 A | 10/1995 | Ryan |
| 5,476,475 A | 12/1995 | Gadberry |
| 5,480,410 A | 1/1996 | Cuschieri et al. |
| 5,496,280 A | 3/1996 | Vandenbrock |
| 5,503,112 A | 4/1996 | Luhman |
| 5,514,109 A | 5/1996 | Mollenauer et al. |
| 5,514,133 A | 5/1996 | Golub et al. |

| | | | | | | |
|---|---|---|---|---|---|---|
| 5,520,632 | A | 5/1996 | Leveen | 6,162,172 A | 12/2000 | Cosgrove et al. |
| 5,522,791 | A | 6/1996 | Leyva | 6,162,196 A | 12/2000 | Hart et al. |
| 5,522,824 | A | 6/1996 | Ashby | 6,162,206 A | 12/2000 | Bindokas |
| 5,524,644 | A | 6/1996 | Crook | 6,163,949 A | 12/2000 | Neuenschwander |
| 5,526,536 | A | 6/1996 | Cartmill | 6,164,279 A | 12/2000 | Tweedle |
| 5,545,179 | A | 8/1996 | Williamson, IV | 6,171,282 B1 | 1/2001 | Ragsdale |
| 5,562,632 | A | 10/1996 | Davila | 6,183,486 B1 | 2/2001 | Snow et al. |
| 5,562,688 | A | 10/1996 | Riza | 6,238,373 B1 | 5/2001 | de la Torre et al. |
| 5,584,850 | A | 12/1996 | Hart et al. | 6,254,533 B1 | 7/2001 | Fadem et al. |
| 5,601,579 | A | 2/1997 | Semertzides | 6,254,534 B1 | 7/2001 | Butler et al. |
| 5,620,415 | A | 4/1997 | Lucey | 6,258,065 B1 | 7/2001 | Dennis |
| 5,632,979 | A | 5/1997 | Goldberg | 6,315,770 B1 | 11/2001 | de la Torre et al. |
| 5,634,911 | A | 6/1997 | Hermann et al. | 6,319,246 B1 | 11/2001 | de la Torre et al. |
| 5,634,936 | A | 6/1997 | Linden | 6,322,541 B2 | 11/2001 | West |
| 5,634,937 | A | 6/1997 | Mollenauer et al. | 6,346,074 B1 | 2/2002 | Roth |
| 5,636,645 | A | 6/1997 | Ou | 6,382,211 B1 | 5/2002 | Crook |
| 5,640,977 | A | 6/1997 | Leahy et al. | 6,420,475 B1 | 7/2002 | Chen |
| 5,649,550 | A | 7/1997 | Crook | 6,440,063 B1 | 8/2002 | Beane |
| 5,653,705 | A | 8/1997 | de la Torre et al. | 6,450,983 B1 | 9/2002 | Rambo |
| 5,657,963 | A | 8/1997 | Hinchliffe | 6,454,783 B1 | 9/2002 | Piskun |
| 5,658,272 | A | 8/1997 | Hasson | 6,485,435 B1 | 11/2002 | Bakal |
| 5,658,306 | A | 8/1997 | Kieturakis | 6,533,734 B1 | 3/2003 | Corley, III et al. |
| 5,672,168 | A | 9/1997 | de la Torre et al. | 6,554,793 B1 | 4/2003 | Pauker |
| 5,685,854 | A | 11/1997 | Green | 6,578,577 B2 | 6/2003 | Bonadio et al. |
| 5,707,703 | A | 1/1998 | Rothrum et al. | 6,582,364 B2 | 6/2003 | Butler et al. |
| 5,709,664 | A | 1/1998 | Vandenbrock | 6,589,167 B1 | 7/2003 | Shimonmura |
| 5,720,730 | A | 2/1998 | Blake, III | 6,589,211 B1 | 7/2003 | MacLeod |
| 5,738,628 | A | 4/1998 | Sierocuk et al. | 6,607,504 B2 | 8/2003 | Haarala |
| 5,741,234 | A | 4/1998 | Aboul-Hosn | 6,613,952 B2 | 9/2003 | Rambo |
| 5,741,298 | A | 4/1998 | MacLeod | 6,623,426 B2 | 9/2003 | Bonadio et al. |
| 5,749,882 | A | 5/1998 | Hart et al. | 6,706,050 B1 | 3/2004 | Giannadakis |
| 5,755,660 | A | 5/1998 | Tyagi | 6,714,298 B2 | 3/2004 | Ryer |
| 5,769,783 | A | 6/1998 | Fowler | 6,723,044 B2 | 4/2004 | Pulford |
| 5,782,812 | A | 7/1998 | Hart et al. | 6,797,765 B2 | 9/2004 | Pearce |
| 5,795,290 | A | 8/1998 | Bridges | 6,814,078 B2 | 11/2004 | Crook |
| 5,803,919 | A | 9/1998 | Hart et al. | 6,814,700 B1 | 11/2004 | Mueller et al. |
| 5,803,921 | A | 9/1998 | Bonadio | 6,840,951 B2 | 1/2005 | de la Torre et al. |
| 5,807,350 | A | 9/1998 | Diaz | 6,846,287 B2 | 1/2005 | Bonadio et al. |
| 5,810,721 | A | 9/1998 | Mueller et al. | 6,866,861 B1 | 3/2005 | Luhman |
| 5,813,409 | A | 9/1998 | Leahy et al. | 6,884,253 B1 | 4/2005 | McFarlane |
| 5,814,026 | A | 9/1998 | Yoon | 6,902,541 B2 | 6/2005 | McNally et al. |
| 5,817,062 | A | 10/1998 | Flom | 6,908,430 B2 | 6/2005 | Caldwell |
| 5,820,555 | A | 10/1998 | Mueller | 6,916,331 B2 | 7/2005 | Mollenauer et al. |
| 5,832,925 | A | 11/1998 | Rothrum | 6,936,037 B2 | 8/2005 | Bubb |
| 5,853,395 | A | 12/1998 | Crook et al. | 6,939,296 B2 | 9/2005 | Ewers |
| 5,871,474 | A | 2/1999 | Hermann et al. | 6,958,037 B2 | 10/2005 | Ewers |
| 5,882,344 | A | 3/1999 | Stouder | 6,979,324 B2 | 12/2005 | Bybordi |
| 5,899,208 | A | 5/1999 | Bonadio | 7,008,377 B2 | 3/2006 | Beane |
| 5,906,577 | A | 5/1999 | Beane et al. | 7,052,454 B2 | 5/2006 | Taylor |
| 5,916,232 | A | 6/1999 | Hart | 2001/0037053 A1 | 11/2001 | Bonadio et al. |
| 5,944,450 | A | 8/1999 | Stevens | 2001/0039430 A1 | 11/2001 | Dubrul et al. |
| 5,947,922 | A | 9/1999 | MacLeod | 2002/0038077 A1 | 3/2002 | de la Torre et al. |
| 5,951,467 | A | 9/1999 | Picha et al. | 2003/0139756 A1 | 7/2003 | Brustad |
| 5,957,913 | A | 9/1999 | de la Torre et al. | 2003/0187376 A1 | 10/2003 | Rambo |
| 5,964,781 | A | 10/1999 | Mollenauer et al. | 2003/0192553 A1 | 10/2003 | Rambo |
| 5,993,485 | A | 11/1999 | Beckers | 2003/0225392 A1 | 12/2003 | McMichael |
| 5,994,450 | A | 11/1999 | Pearce | 2004/0024363 A1 | 2/2004 | Goldberg |
| 5,997,515 | A | 12/1999 | de la Torre et al. | 2004/0049100 A1 | 3/2004 | Butler |
| 6,024,736 | A | 2/2000 | de la Torre et al. | 2004/0073090 A1 | 4/2004 | Butler et al. |
| 6,025,067 | A | 2/2000 | Fay | 2004/0092796 A1 | 5/2004 | Butler et al. |
| 6,033,426 | A | 3/2000 | Kaji | 2004/0093018 A1 | 5/2004 | Johnson |
| 6,033,428 | A | 3/2000 | Sardella | 2004/0106942 A1 | 6/2004 | Taylor |
| 6,042,573 | A | 3/2000 | Lucey | 2004/0143158 A1 | 7/2004 | Hart et al. |
| 6,044,295 | A | 3/2000 | Mueller | 2004/0215063 A1 | 10/2004 | Bonadio et al. |
| 6,048,309 | A | 4/2000 | Flom et al. | 2005/0020884 A1 | 1/2005 | Heart et al. |
| 6,059,816 | A | 5/2000 | Moenning | 2005/0033246 A1 | 2/2005 | Ahlberg |
| 6,077,288 | A | 6/2000 | Shimomura et al. | 2005/0059865 A1 | 3/2005 | Kahle |
| 6,110,154 | A | 8/2000 | Shimomura et al. | 2005/0065543 A1 | 3/2005 | Kahle |
| 6,123,689 | A | 9/2000 | To | 2005/0090713 A1 | 4/2005 | Gozales |
| 6,142,935 | A | 11/2000 | Flom et al. | 2005/0090717 A1 | 4/2005 | Bonadio et al. |
| 6,142,936 | A | 11/2000 | Beane et al. | 2005/0131349 A1 | 6/2005 | Albrecht |
| 6,150,608 | A | 11/2000 | Wambeke | 2005/0148823 A1 | 7/2005 | Vaugh et al. |
| 6,159,182 | A | 12/2000 | Davis | 2005/0159647 A1 | 7/2005 | Hart et al. |

| | | | |
|---|---|---|---|
| 2005/0192598 A1 | 9/2005 | Johnson | |
| 2005/0241647 A1 | 11/2005 | Nguyen | |
| 2005/0277946 A1 | 12/2005 | Greenhalgh | |
| 2005/0288558 A1 | 12/2005 | Ewers | |
| 2005/0288634 A1 | 12/2005 | O'Herron | |
| 2006/0041270 A1 | 2/2006 | Lenker | |
| 2006/0047284 A1 | 3/2006 | Gresham | |
| 2006/0106402 A1 | 5/2006 | McLucas | |
| 2006/0149306 A1 | 7/2006 | Hart et al. | |

FOREIGN PATENT DOCUMENTS

| | | |
|---|---|---|
| DE | 37 37 121 | 5/1989 |
| DE | 296 00 939 | 6/1998 |
| EP | 0142262 | 5/1985 |
| EP | 0537768 | 4/1993 |
| EP | 0950376 | 10/1999 |
| EP | 1118657 | 7/2001 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1496696 | 12/1977 |
| GB | 2071502 | 9/1981 |
| GB | 2255019 | 10/1992 |
| GB | 2275420 | 8/1994 |
| JP | 10-108868 | 4/1998 |
| JP | 2001-061850 | 3/2001 |
| JP | 2004-195037 | 7/2004 |
| RU | 1342485 | 1/1997 |
| WO | WO 86/06272 | 11/1986 |
| WO | WO 92/11880 | 7/1992 |
| WO | WO 92/21292 | 12/1992 |
| WO | WO 93/05740 | 4/1993 |
| WO | WO 95/05207 | 2/1995 |
| WO | WO 95/07056 | 3/1995 |
| WO | WO 95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/32514 | 9/1997 |
| WO | WO 97/32515 | 9/1997 |
| WO | WO 98/35614 | 9/1998 |
| WO | WO 98/48724 | 11/1998 |
| WO | WO 99/03416 | 1/1999 |
| WO | WO 99/25268 | 5/1999 |
| WO | WO 99/29250 | 6/1999 |
| WO | WO 00/32116 | 6/2000 |
| WO | WO 00/32117 | 6/2000 |
| WO | WO 00/32119 | 6/2000 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |
| WO | WO 01/26558 | 4/2001 |
| WO | WO 01/91652 | 12/2001 |
| WO | WO 02/34108 A2 | 5/2002 |
| WO | WO 03/034908 A3 | 5/2003 |
| WO | WO 03/061480 A1 | 7/2003 |
| WO | WO 03/103548 A1 | 12/2003 |
| WO | WO 2004/026153 A1 | 4/2004 |
| WO | WO 2004/030547 A1 | 4/2004 |
| WO | WO 2005/009257 A2 | 2/2005 |

* cited by examiner

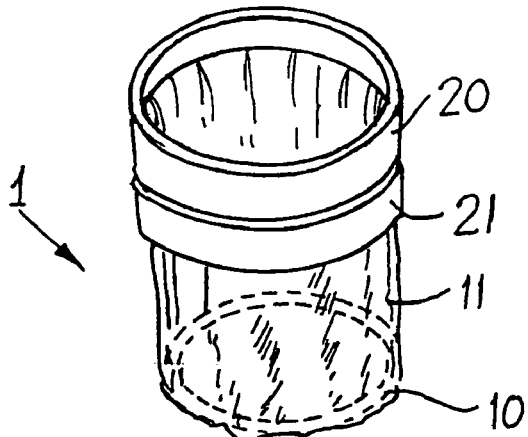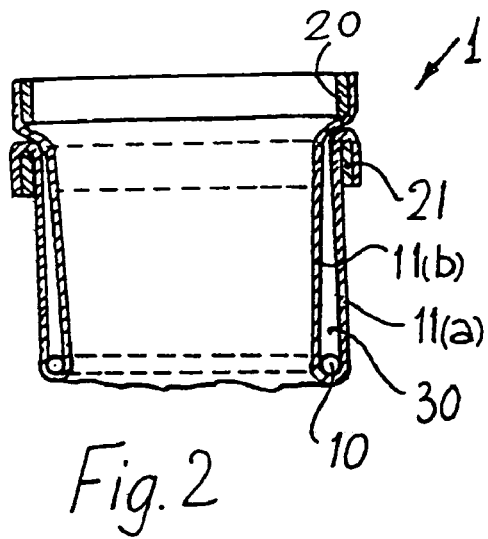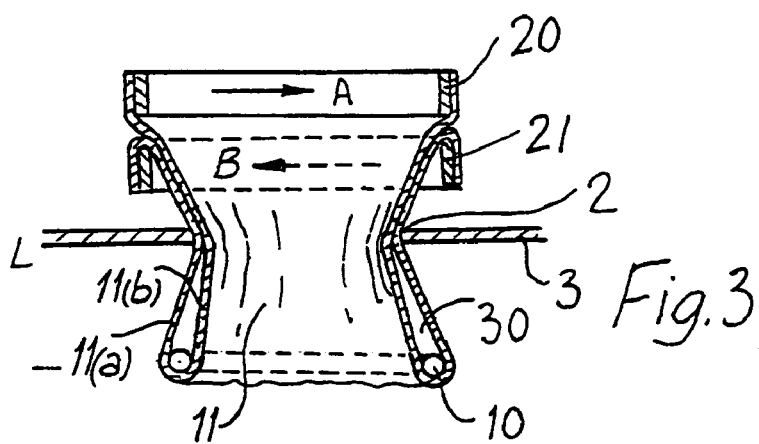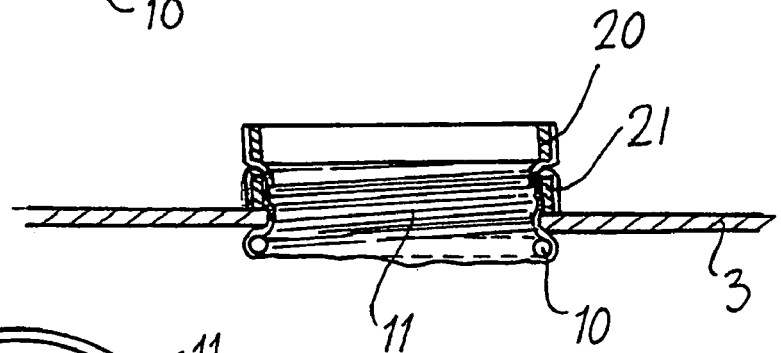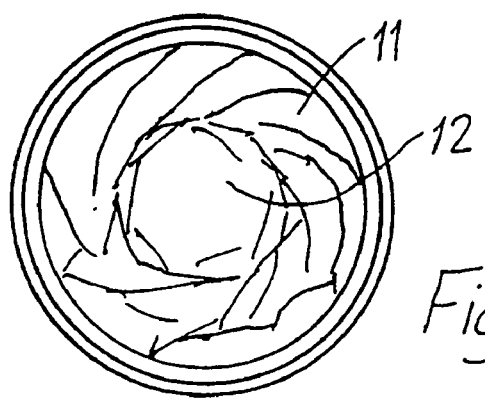

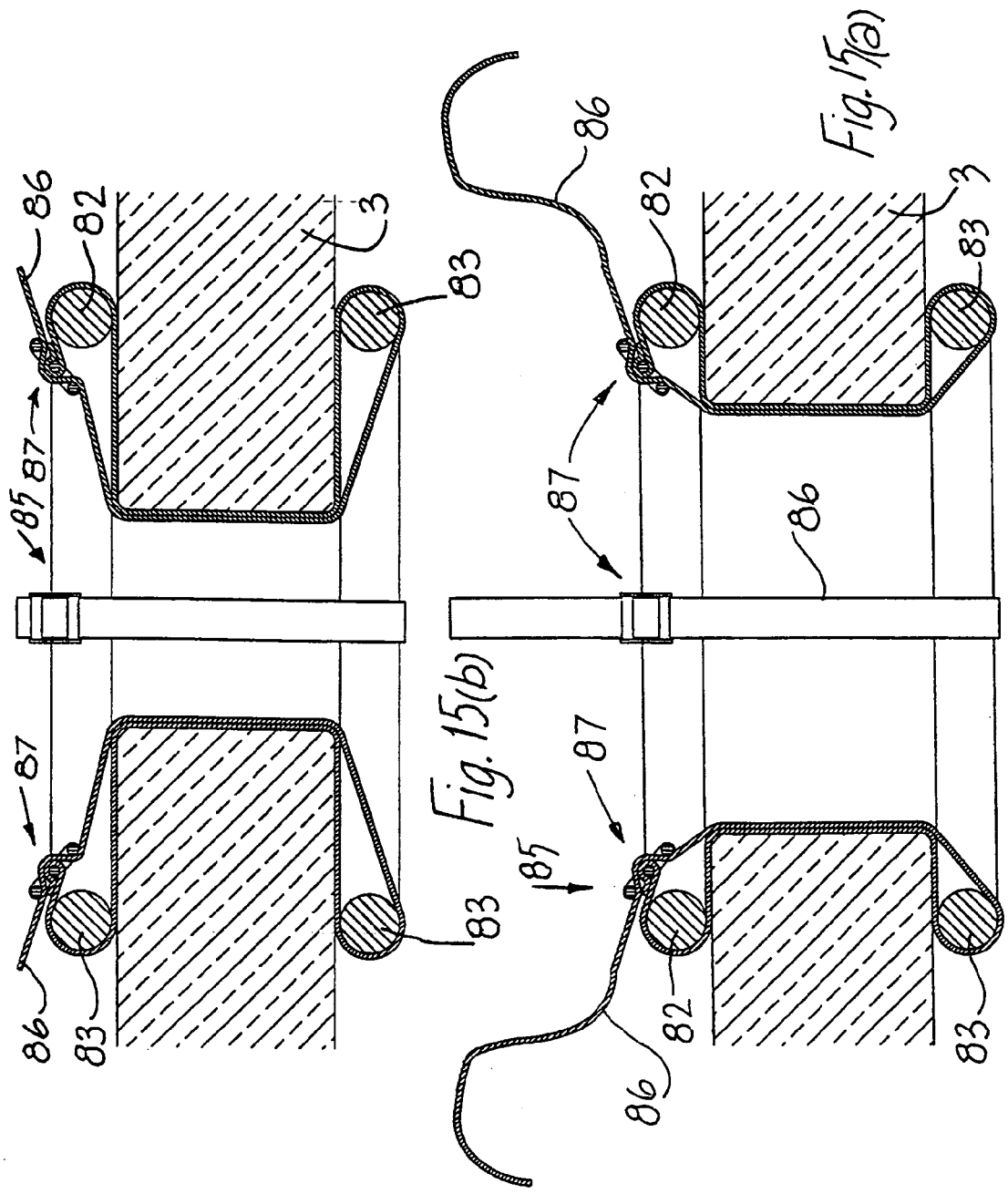

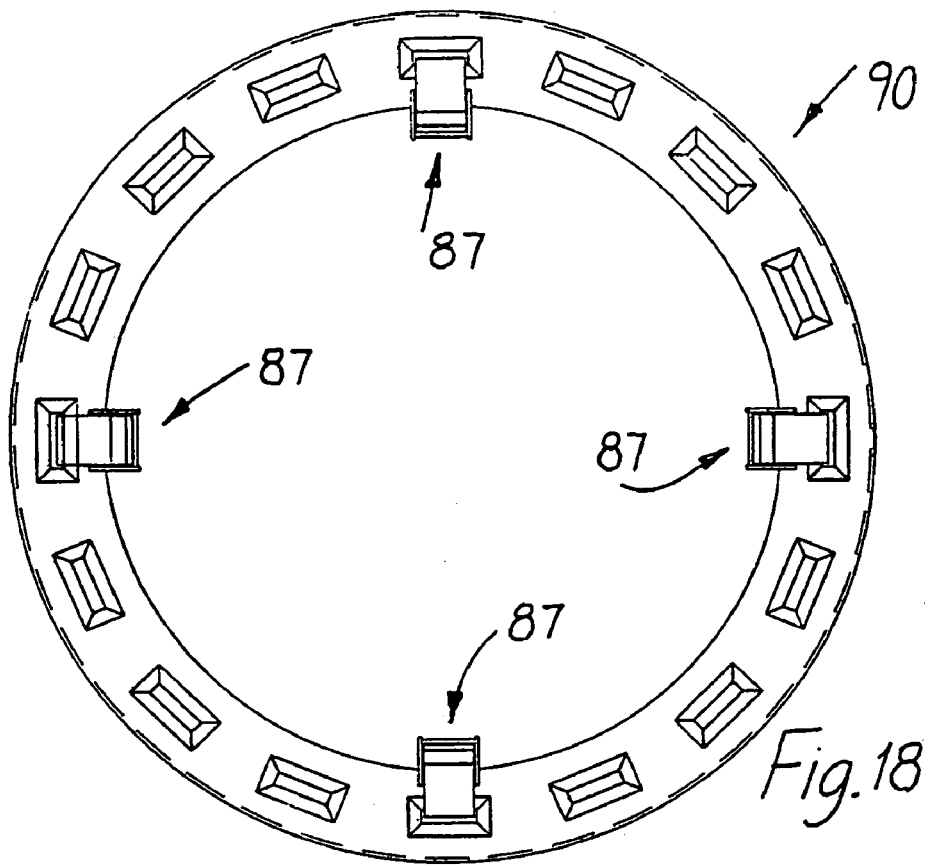
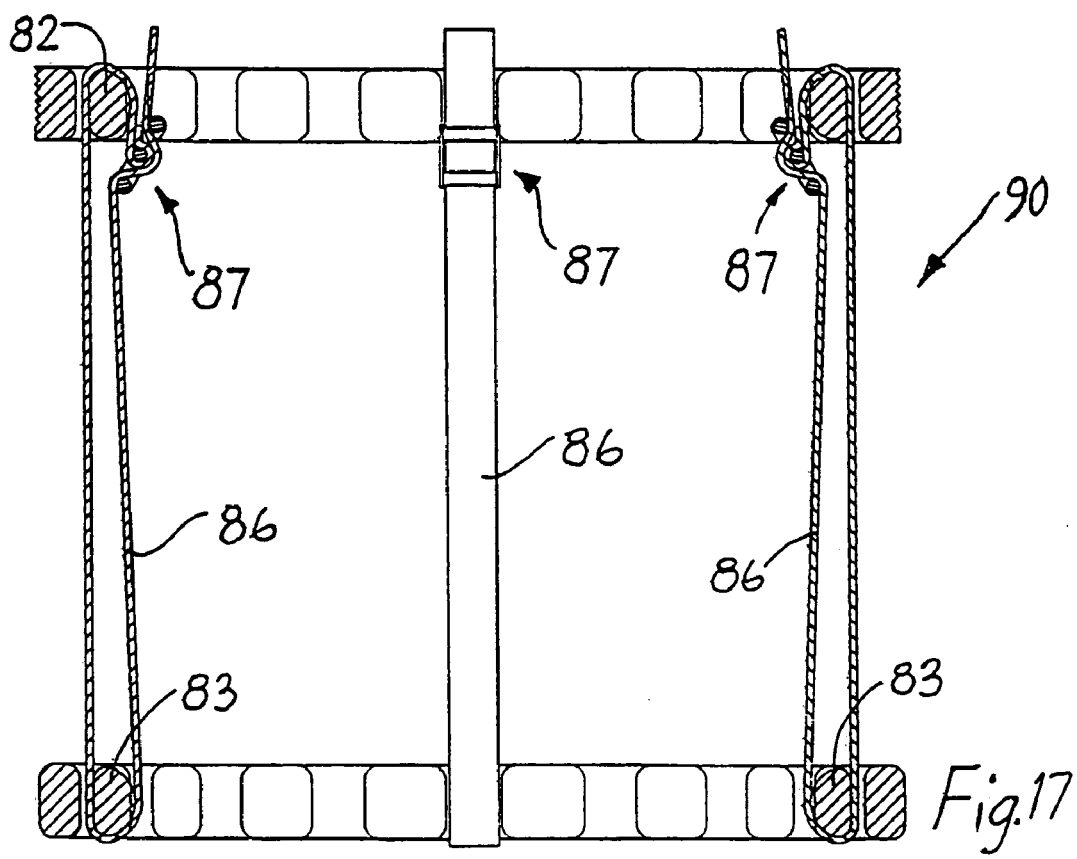

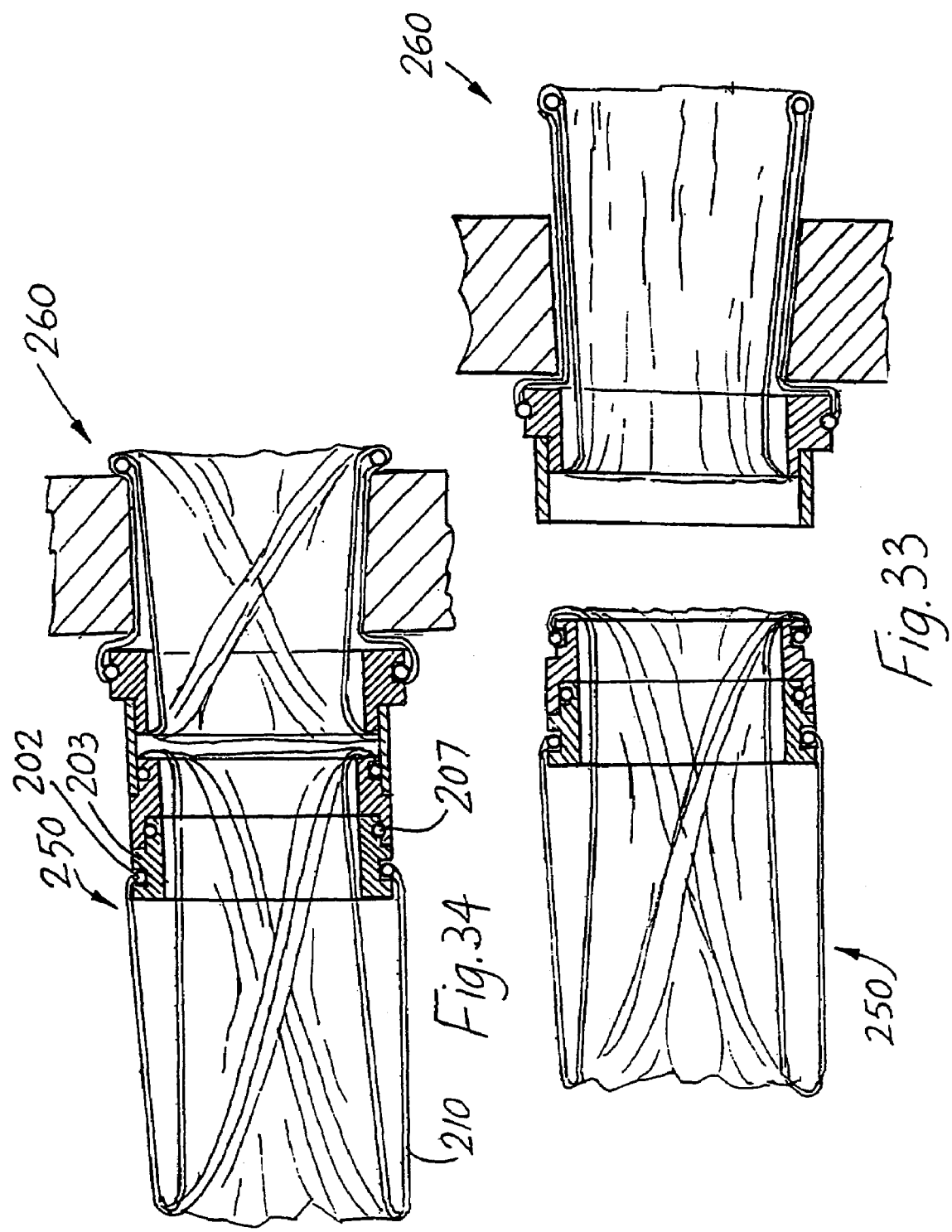

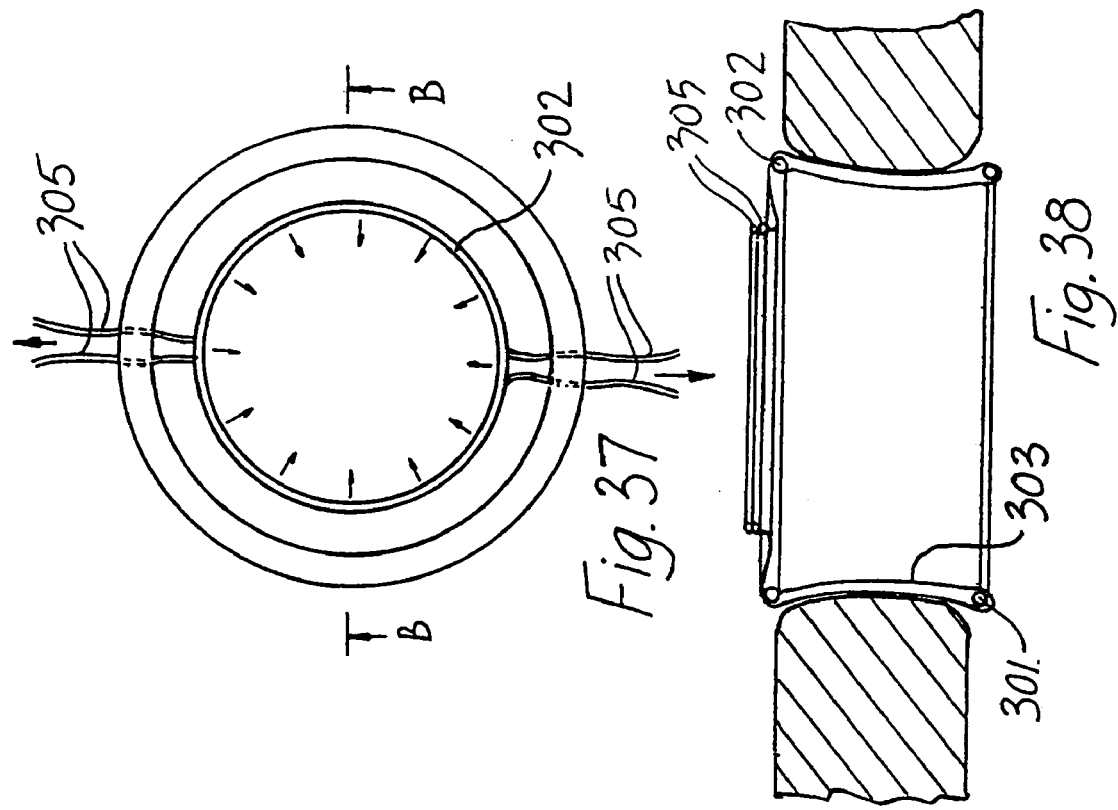
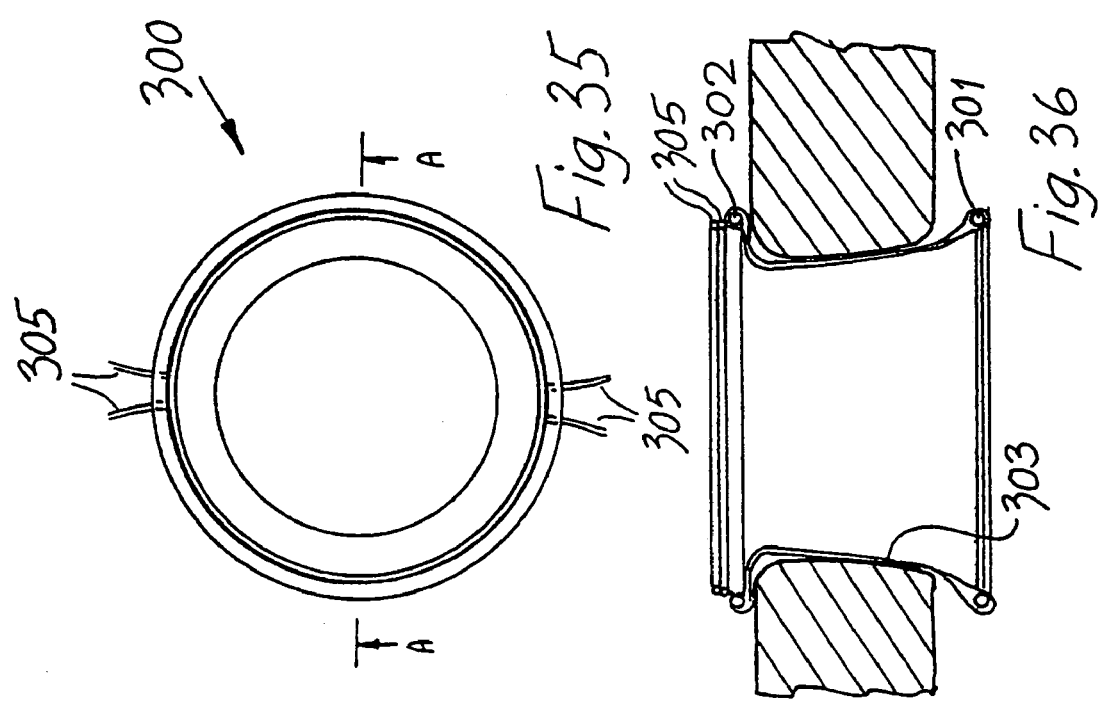

SURGICAL DEVICE FOR RETRACTING AND/OR SEALING AN INCISION

CROSS REFERENCE TO RELATED APPLICATIONS

This is a continuation of U.S. application Ser. No. 10/133,979, filed Apr. 29, 2002 now U.S. Pat. No. 6,846,287, which is a continuation of U.S. application Ser. No. 09/801,826, filed Mar. 9, 2001, now abandoned, which is a continuation of PCT International Application No. PCT/IE99/00122, filed Dec. 1, 1999, all of which are incorporated herein by reference.

BACKGROUND OF THE INVENTION

The present invention relates to a surgical device. More specifically, the invention relates to devices for retraction of an incision or natural bodily opening during surgery and for protecting the edges of incisions from infection or tumour seeding during surgery.

Wound Retraction

Adequate anatomical exposure is required in modern surgical procedures to allow procedures to be safely and effectively performed. Anatomical exposure is achieved by separating the walls of a natural orifice or spreading apart the margins of a surgical incision. A difficult surgical procedure can be simplified by adequate retraction whereas a relatively simple procedure can be made more difficult or even dangerous by the lack of adequate retraction. Exposure is maximised with correct incision placement and well directed retraction.

Retraction can be achieved in several different ways. The most common method of surgical wound retraction is by the use of hand held retractors. These may be made of metal or thermoplastics and allow an operator to apply a retraction force to the wound edges. They are disposable or reusable and come in a variety of shapes and sizes to satisfy the requirements of different surgical procedures.

Another type of retractor are Frame mounted retractor devices are also known. Such devices consist of a rigid circular or horseshoe-shaped frame on which multiple, detachable and movable paddle retractors are attached. The device may be mounted to an operating table to provide secure anchorage. Retraction may be applied in required directions. Typically such retractors are made of stainless steel to facilitate cleaning and sterilisation for reuse. Some of the more complex retractors need to be taken apart before sterilisation and reassembled before use. These devices always apply retraction at a fewspecific locations on the wound. This is a disadvantage of such devices as it can lead to regional ischaemia on parts the wound edge.

A wound retractor and protector is disclosed in U.S. Pat. No. 5,524,644 (Crook). This device consists of an open-ended sleeve of polymeric material with a flexible ring at each end. One ring is inserted into the incision and the sleeve is manually rolled up around the other ring to apply tension to the polymeric material to achieve retraction. The device is often difficult to use because of the manual dexterity required, especially when the surgeons hands are wet. In addition, the device is incrementally adjustable. This restricts the efficiency of the device across all abdominal wall thicknesses.

U.S. Pat. No. 5,545,179 (Williamson IV) describes a device having an elastomeric sealing element and a tubing conduit. The device protects the edges of the wound from contamination. However, the device is specifically for laparoscopic instruments and is not suitable for hand assisted surgery because the wound opening is not sufficiently retracted.

WO-A-96/36283 (Mollenauer) describes a trocar device for retracting and sealing an incision and providing a sealed access port for surgical instruments. Whilst this incision and providing a sealed access port for surgical instruments. Whilst this device provides both retraction and protection to the wound edge is not suitable for use in hand assisted surgery due to size limitations. The device retarcts and protects due to the inflation of one or one or more balloons and because these close the lumen when inflated it is not possible to visulaise the contents of the abdomen through the device.

WO-A-98/48724 discloses a device for use in hand assisted laparoscopic surgery. The device has a wound retractor/protector component and a component for sealing around the wrist of the surgeon. The wound protector component consists of an inner ring and two outer inflatable doughnut-shaped rings mounted vertically on top of another. The inner and outer rings are linked by an elastomeric sleeve. Inflation of the two outer rings causes retraction of the elastomeric sleeve. This device provides wound retraction and protection but it is not suitable for device has a large vertical profile due to the outer rings. This restructs reach into the incision and extends the fulcrum of any instruments used in such a way that their effective reach and breath of lateral movement would be severely restricted.

Wound Protection

The sides of an open wound are susceptible to infection and cross contamination if they are touched by contaminated material such as body parts or fluids as they pass through the opening of a wound. Serious problems can also result from cancerous material coming into contact with the wound edge. It is well known that cancerous cells may become seeded in wound areas, especially at trocar sites.

To avoid such problems great care is taken to protect the edges of an incision using drapes that are impervious to liquids. An incision liner is disclosed in U.S. Pat. No. 3,397,692 (Creager). This linear comprises a sheet of polymeric material. The sheet has a hole cut out in the centre and the edges of the hole are reinforced using a semi-rigid ring. This ring can be inserted into the incision allowing a surgical procedure to proceed through the ring while the material attached to the ring protects the edges of the incision from contaminants in the wound site. These device marketed as "Steridrape" by 3M Corporation and comes in a variety of sizes for different wound sizes. However such devices do not adequately retract an incision.

In general known devices are of either complex construction, do not effectively seal a wound and/or are difficult to operate.

There is therefore a need for an improved surgical device that will overcome at least some of these problems.

STATEMENTS OF INVENTION

According to the invention there is provided a surgical device comprising:
  an inner mounting means for insertion through a wound opening;
  a first outer mounting means for mounting external of a wound opening; and
  connecting means extending between the inner and outer mounting means;

the connecting means being movable to shorten the axial extent of the connecting means.

In a particularly preferred embodiment of the invention the outer mounting means is movable relative to the inner mounting means to twist the connecting means to form a lumen of reduced cross section and to shorten the axial extent of the connecting means.

Most preferably the outer mounting means is rotatable relative to the inner mounting means to twist the connecting means.

In a particularly preferred embodiment of the invention the connecting means is a sleeve of pliable material extending between the inner and outer mounting means.

In one aspect the device includes a second outer mounting means, the connecting means extending between the first outer mounting means, the inner mounting means, and the second outer mounting means.

In this case preferably the first and second outer mounting means are rotatable relative to one another to twist the connecting means and to draw the inner mounting means towards the outer mounting means. The outer rings also rotate relative to the inner mounting means.

In a particularly preferred embodiment the inner mounting means is an O-ring; Preferably the connecting means is a sleeve which is led from the first outer mounting means to the O-ring and from the O-ring to the second outer mounting means.

In a preferred embodiment of the invention the device includes locking means for locking the first outer mounting means relative to the second outer mounting means.

In one arrangement one of the outer mounting means is located or locatable within the other outer mounting means.

Preferably the inner diameter of the sleeve is greater than or equal to the axial length of the sleeve.

In a preferred arrangement the inner diameter of the sleeve is greater than the axial length of the sleeve by an amount less than the thickness of an average abdominal wall, which is typically 2 to 6 cm. This assists in achieving a retraction force.

Preferably a substantially gas tight seal is formed between the outer mounting means on shortening of the length of the sleeve. Ideally, the sleeve extending between the first and second outer mounting means defines an inflatable space.

In one embodiment of the invention the device includes a port for connection to an inflation means.

The invention also provides a surgical device comprising:
an inner mounting means for insertion through a wound opening;
a first outer mounting means;
a second outer mounting means; and
a sleeve of pliable material extending from the second outer mounting means to the inner mounting means and from the inner mounting means to the first outer mounting means.

Preferably one or both of the first and second outer mounting means are movable relative to one another to adjust the diameter of the lumen defined by a twist in the sleeve extending therebetween.

Ideally, the first and second outer mounting means are rotatable relative to one another.

In one embodiment of the invention the sleeve is releasably mounted to the second outer mounting means for adjustment of the length of the sleeve.

Preferably the second mounting means comprises a receiver and the sleeve is mounted or mountable to a ring which is releasably mounted to the receiver.

In another embodiment of the invention the inner mounting means is configured to reduce the size thereof for ease of insertion into a wound opening.

Typically in this case the inner mounting means comprises a ring which includes a hinge means for reducing the size of the ring.

A device wherein the connecting means is translated to shorten the axial extent of the connecting means.

A device wherein the connecting means comprises a sleeve which is translated by a drawstring mechanism.

A device wherein the connecting means comprises a plurality of straps attached to the inner mounting means, the straps being pulled upwardly to shorten the axial extend of the connecting means.

Typically the outer mounting means includes a holder for holding a surgical instrument.

The surgical device may form a wound retractor, a wound protector or a wound protector retractor.

BRIEF DESCRIPTION OF DRAWINGS

The invention will be more clearly understood from the following description thereof given by way of example only with reference to the accompanying drawings, in which:

FIG. 1 is a perspective view of a surgical device according to the invention;

FIG. 2 is a cross sectional view of the device of FIG. 1;

FIG. 3 is a cross sectional view of the device in one position of use;

FIG. 4 is a cross sectional view of the device in another position of use;

FIG. 5 is a top plan view of the device in the position of FIG. 4;

FIGS. 15A and 15B are cross sectional views of the device of FIG. 14, in use;

FIG. 17 is a cross section view of another surgical device of invention;

FIG. 18 is a plan view of the device of FIG. 17;

FIG. 33 is a cross sectional view of two surgical devices ready for assembly;

FIG. 34 is a cross sectional view of the devices of FIG. 33, assembled;

FIG. 35 is a plan view of another surgical device according to the invention;

FIG. 36 is a cross sectional view on the line A-A in FIG. 35 with the device in position in an incision;

FIG. 37 is a plan view of the device of FIGS. 35 and 36 in another position of use; and FIG. 38 is a cross sectional view on the line B-B of FIG. 37.

DETAILED DESCRIPTION

Figure 7:
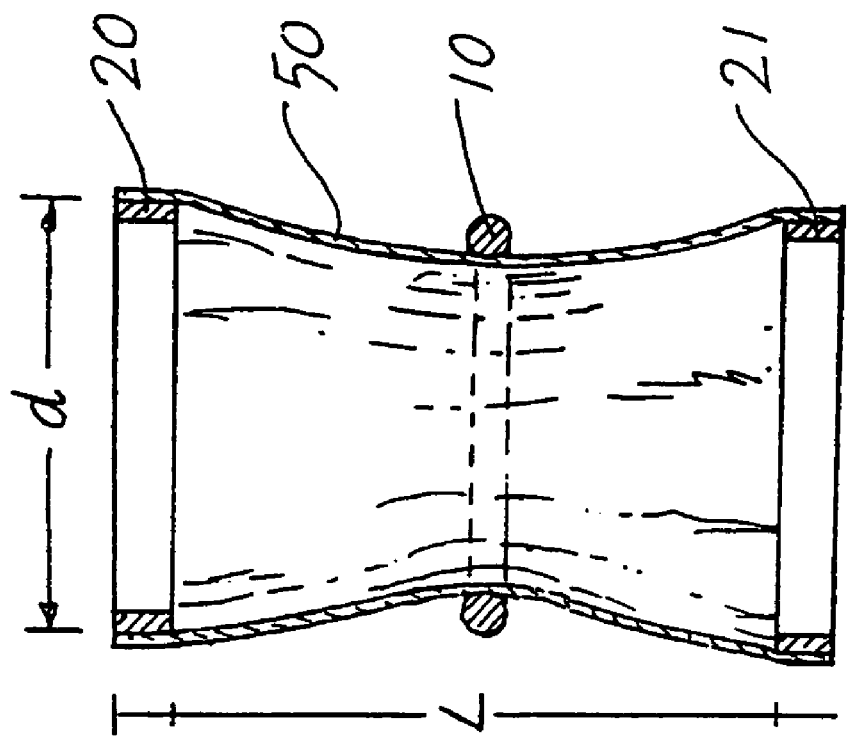
FIGS. 6 and 7 are respectively perspective and cross sectional views illustrating a method of forming the device of FIGS. 1 to 5.

Referring to the drawings and initially to FIG. 1 to 7 thereof there is illustrated a surgical device, especially for use in laproscopic surgery. The device 1 in this case is used in surgery involving an incision 2 in a wall 3 of a patients abdomen. The wound is, in this case, both protected and retracted by the device 1 of the invention. Thus, the invention in this case provides a wound protector retractor.

The device 1 comprises an inner mounting means in the form of an O-ring 10 of flexible material such as of elastomeric material for insertion through the wound opening 2, an outer mounting means for mounting external of the wound opening 2 and a connecting means, in-this-case in the form of a sleeve 11 extending between the inner 10 and outer mounting means. The outer mounting means is movable, in this case rotatable, relative to the inner O-ring 10 to twist the sleeve 11 to form a centralised lumen 12 of reduced cross section and to shorten the axial extent of the sleeve 11. As the sleeve 11 is twisted the inner O-ring 10 is drawn upwardly from the inserted position illustrated in FIG. 3 to the in-use position illustrated in FIG. 4 in which the wound is sealed and a radial retraction force is applied to the wound. A surgeon inserts a sealed gloved hand/arm/instrument through the sealed and retracted wound to perform a surgical procedure within the abdomen.

In this preferred case the outer mounting means comprises a first outer mounting means in the form of a first annular ring 20 and a second outer mounting means in the form of a second annular ring 21. The sleeve 11 is of biocompatible pliable gas impermeable plastics material and is attached at one end to the ring 20 and at an opposite end to the ring 21. The sleeve 11 is connected to the ring 20, led over the O-ring 10 and back up for attachment to the ring 21 as best illustrated in FIG. 2.

In use, a surgeon makes an incision in the abdominal cavity and the O-ring 10 is flexed and inserted through the incision as illustrated in FIG. 3. The outer rings 20, 21 are then rotated relative to one another in the direction of the arrows A and B in FIG. 3. This relative rotation twists the sleeve 11 and shortens the sleeve until the device is in the operative position of FIG. 4. In this position the inner O-ring 10 is engaged against the inside of the interior of the anterior abdominal wall and the rings 21 and 22 are external of the wound opening with the sleeve 11 shortened in axial extent. The twisting of the sleeve 11 provides a central lumen 12 of reduced size, which depends on the degree of twist. A full 180° relative twist would result in closing down of the lumen. The reduced lumen 12 provides access for instruments and/or a surgeons arm while maintaining a wound seal.

Locking means of any suitable type may be provided to lock the rings 20, 21 together. The locking means may, for example comprise a releasable latching system such as a ratchet and pawl arrangement or the like.

Preferably a gas tight seal is formed between the rings 20, 21 in use. The sleeve in this case provides an inflatable space 30 between the rings 20, 21 and the inner O-ring 10. An inflation connection port may be provided in the device to facilitate inflation. On inflation, a wound engaging section 11a of the sleeve is pushed radially outwardly to provide a highly efficient wound protector/seal and wound retractor. The inner sleeve section 11b is inflated to further restrict the lumen 12 and provide highly efficient sealing engagement with a surgeons forearm, a device or an instrument inserted through the lumen.

For efficient sealing engagement it is preferred that the inner diameter (d) of the sleeve 11 is greater than or equal to the axial length (l) of the sleeve 11 as illustrated in FIG. 7. Preferably the inner diameter of the sleeve is greater than the axial length of the sleeve by an amount which is less than the thickness of an average abdominal wall. With this configuration on twisting of the sleeve 11, sealing and retraction forces are applied to the wound opening.

Figure 6:
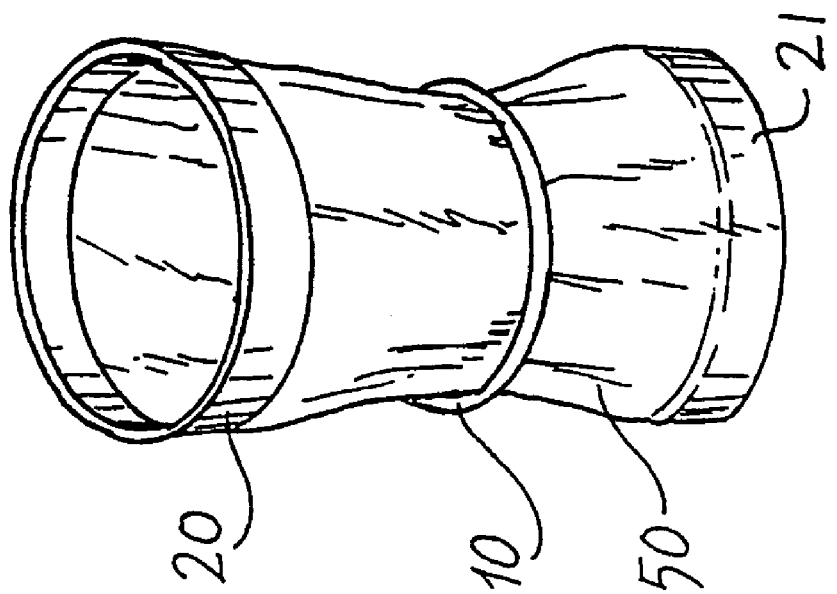

The surgical device 1 may be formed from a cylindrical sleeve 50 of pliable plastic material attached to a pair of rings 20, 21 as illustrated in FIGS. 6 and 7. A flexible O-ring 10 is fitted over the sleeve 50. The flexible sleeve 50 is then turned over on itself so that the O-ring 10 is confined between inner and outer sleeve sections 11a, 11b and the rings 20, 21 are in the configuration illustrated in FIGS. 1 and 2.

The device of the invention applies a force to the wound edges to achieve adequate exposure without causing ischaemic injury to the wound edges. The device protects wound edges from cross infection or seeding by cancerous or otherwise malignant cells. Another advantage is that the device is sufficiently inexpensive that it can be disposed of after a single use thereby obviating the need for cleaning and sterilisation between use. In addition, the device is simple to place into a desired position in a wound or natural bodily opening and easy to remove, especially without negating the benefits gained from use of the device as a wound protector.

Figure 8:
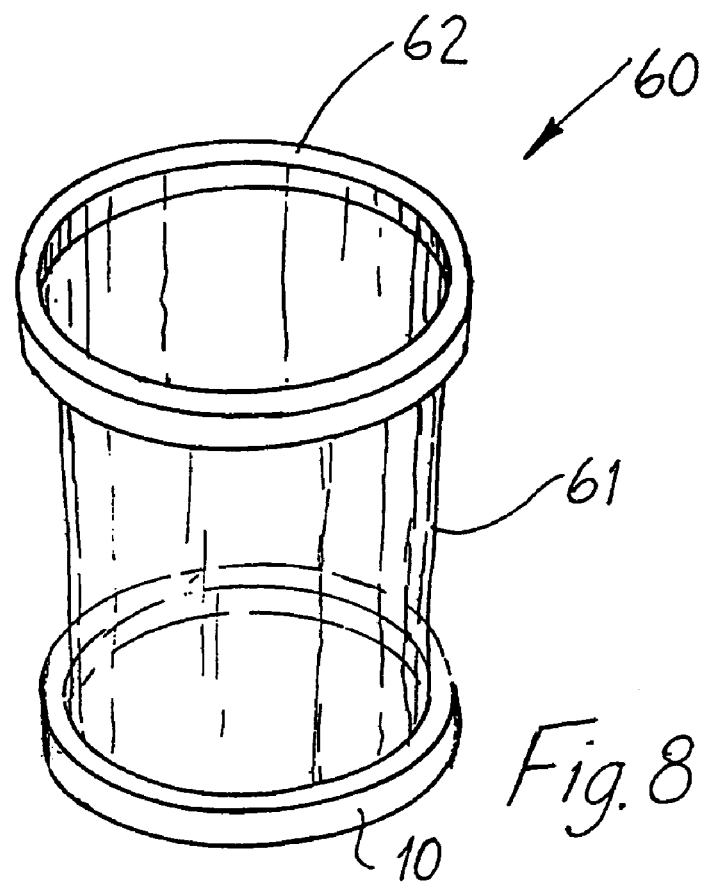
FIG. 8 is a perspective view of another surgical device according to the invention.
Figure 9:
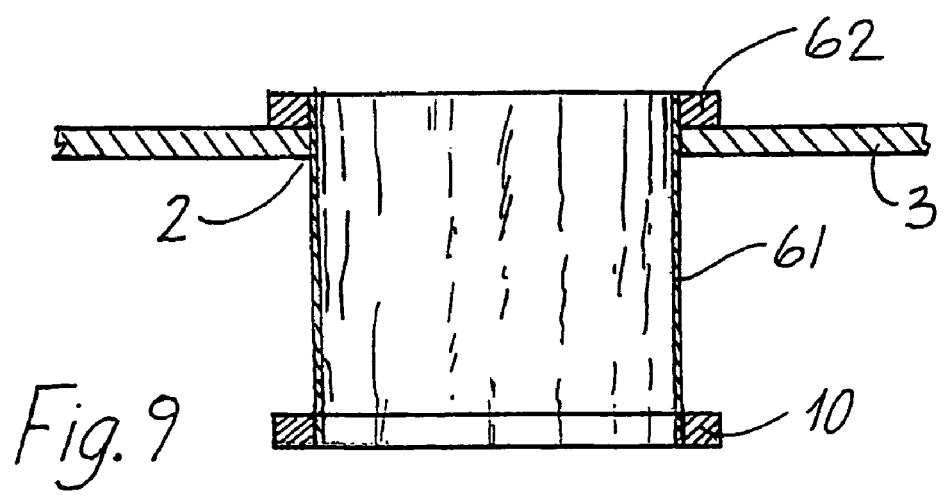
FIG. 9 is a cross sectional view of the device of FIG. 8 in one position of use.
Figure 10:
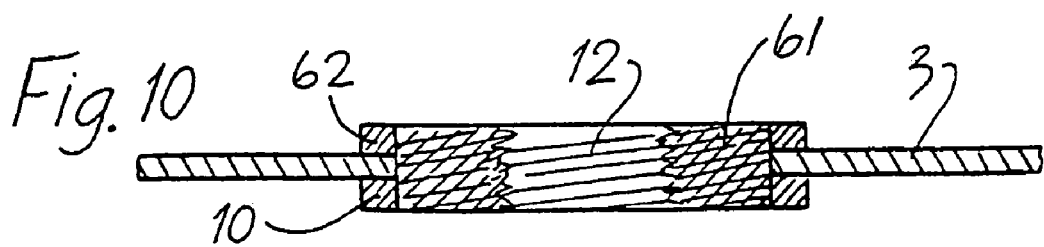
FIG. 10 is a cross sectional view of the device of FIG. 8 in another position of use.

Referring to FIGS. 8 to 10 there is illustrated another surgical device 60 according to the invention. The device 60 is similar to the device 1 and like parts are assigned the same reference numerals. In this case the sleeve 61 is a single wall sleeve and there is only one outer mounting ring 62. On rotation of the outer ring 62 relative to the inner ring 10 a twist is formed in the sleeve which is shortened, drawing the inner ring 10 upwardly against the interior of the anterior abdominal wall as illustrated in FIGS. 9 and 10.

It will be appreciated that the inner O-ring may be fixed, for example, by adhesives to the sleeve of the surgical device. It will also be appreciated that one or more of the mounting means may be shaped to positively engage with tissue. For example, the mounting means may include tissue-engaging projections to lock the mounting means in position.

It will be appreciated that while for efficient retraction and wound protection it is preferred that the connecting means between the outer and inner mounting means is in the form of a sleeve of pliable material, the connecting means may be discontinuous. For example the sleeve may be in the form of elongate strips or the like.

Figure 13:
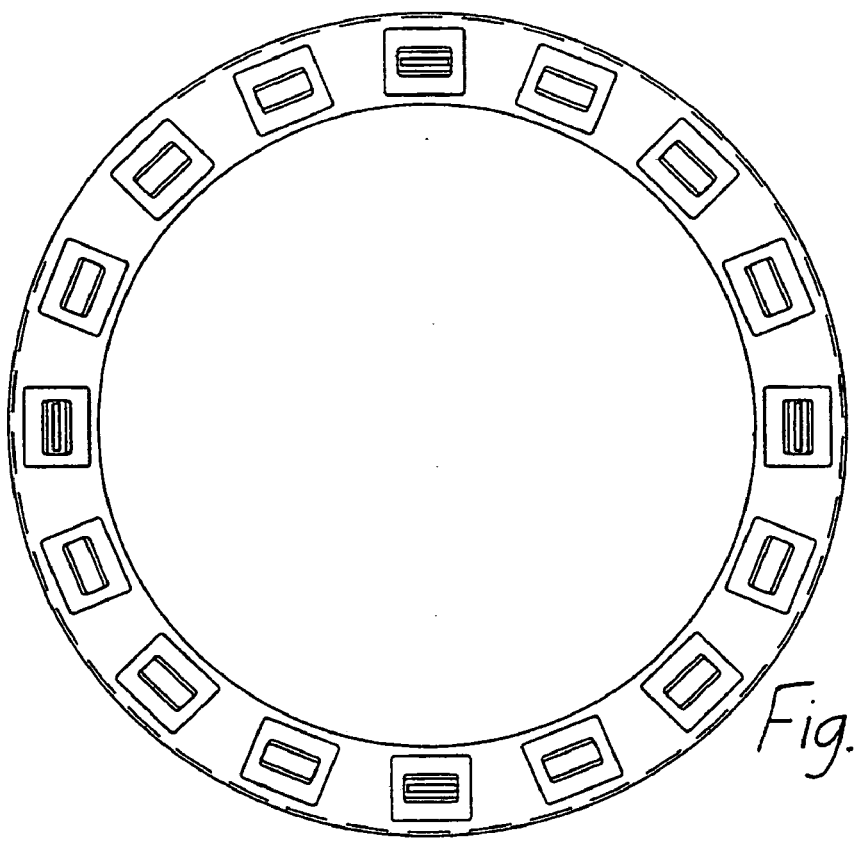
FIG. 13 is a plan view of the device of FIG. 11.
Figure 11:
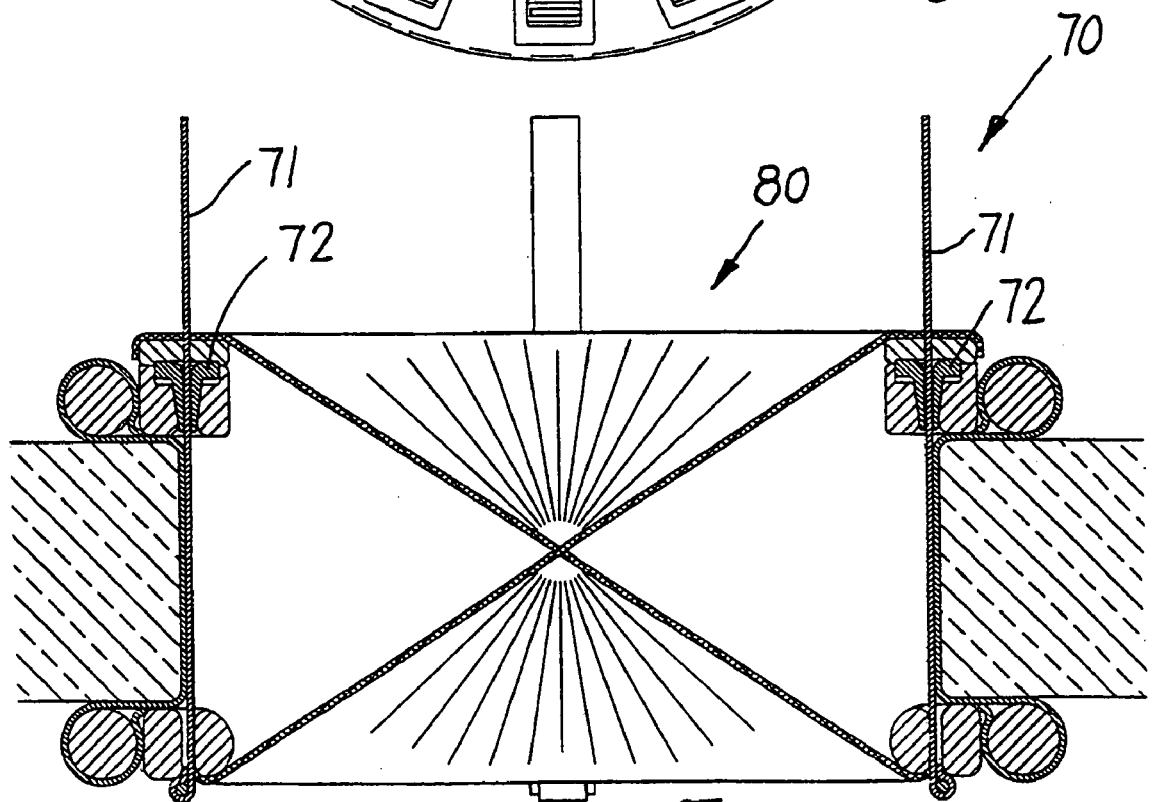
FIGS. 11 and 12 are cross sectional views of another surgical device according to the invention in different positions of use.
Figure 12:
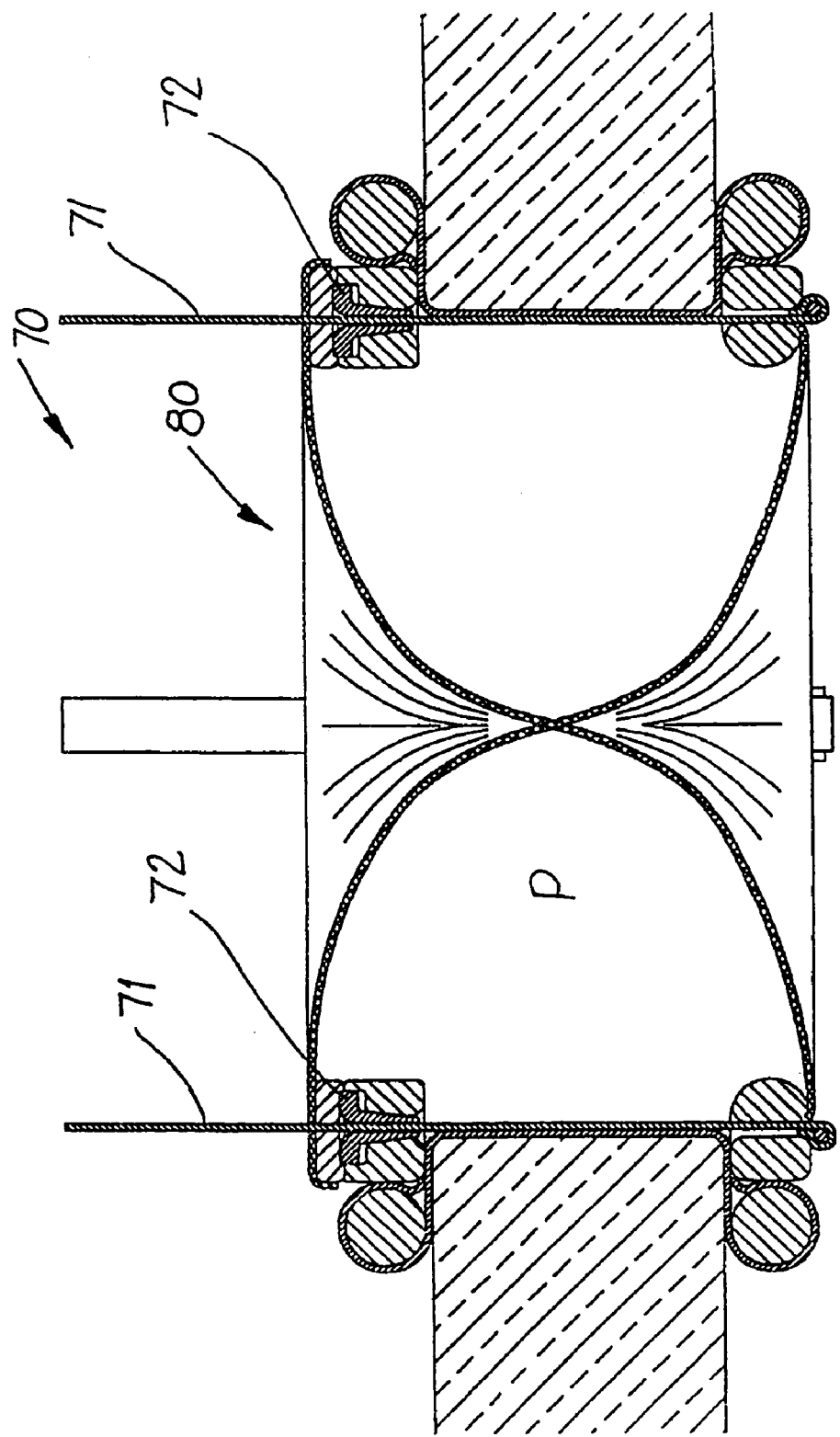

Referring to FIGS. 11 to 13 there is illustrated another surgical device 70 according to the invention. In this case the connecting means comprises a plurality of straps 71 which are drawn upwardly to shorten the axial extent and to form a wound retractor. The straps 71 are retained in the shortened configuration illustrated by any suitable locking means such as by wedge elements 72. In this case an iris diaphragm type device 80 is provided in the wound opening which is inflatable from the rest configuration illustrated in FIG. 11 to the pressurised inflated configuration illustrated in FIG. 12.

Figure 16:
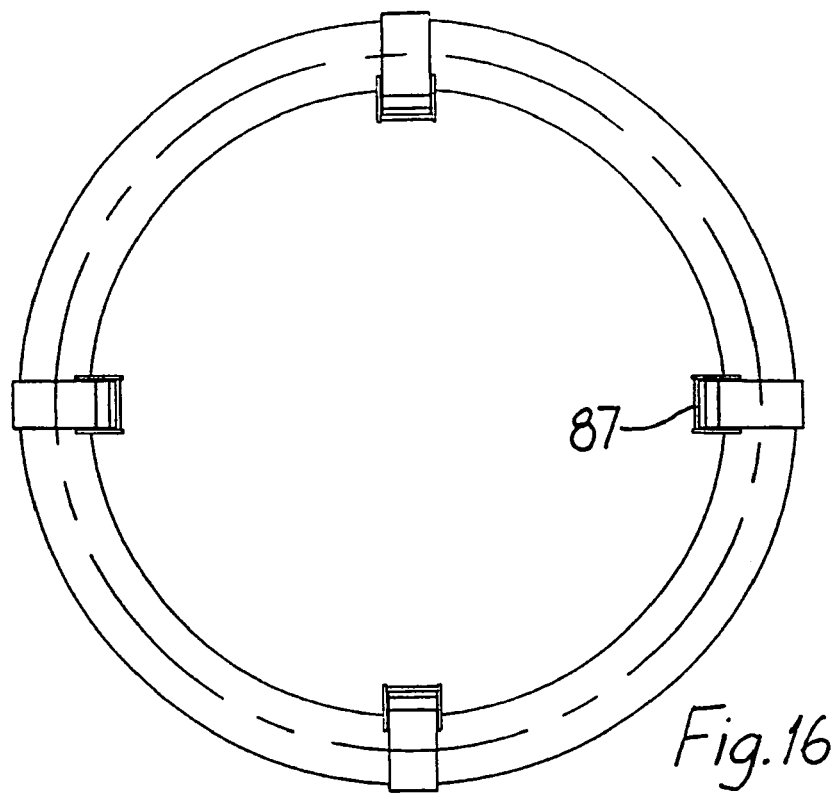
FIG. 16 is plan view of the device of FIG. 14.
Figure 14:
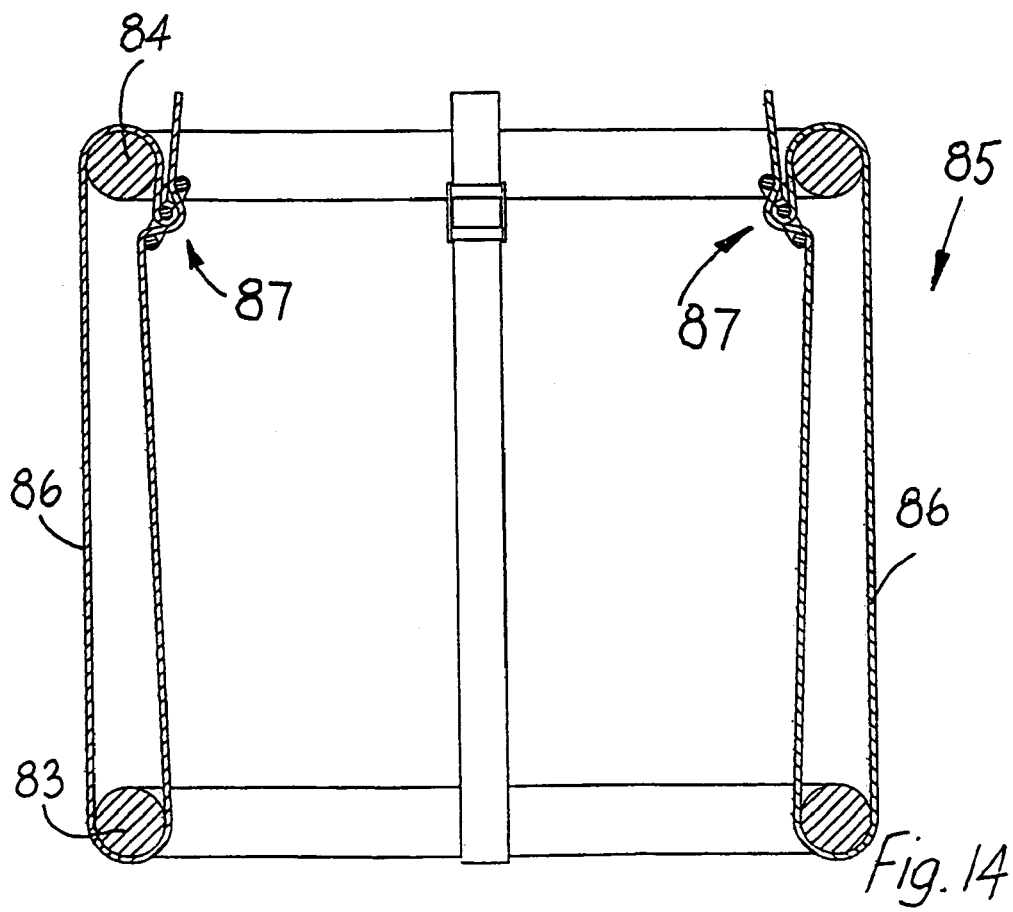
FIG. 14 is a cross sectional view of a further surgical device according to the invention.

Referring to FIGS. 14 to 16 there is illustrated another device 85 according to the invention in which the connecting means is defined by a plurality of straps 86 which are movable between an inner mounting ring 83 and an outer mounting ring 84 by buckle devices 87 from the initial position illustrated in FIG. 15B to the wound retracting position of FIG. 15A. The inner ring 83 is first inserted though the incision. The outer ring 82 is then brought down to skin level by taking up the slack in the straps 86. To achieve the retraction effect the straps 86 are pulled taut causing the wound edge to be displaced out from the centrepoint of the wound. The straps 86 may be adjusted until optimum retraction is achieved. Tension in the straps 86 is maintained by the buckles 86 which may hold the strap 86 taut either by friction or using a clasp mechanism.

Referring to FIGS. 17 and 18 another surgical device 90 similar to the device 85 is illustrated. In this case the inner and outer mounting rings 82, 83 are of oval shape in transverse cross section to smooth the movement of the straps 86. This device operates in a similar manner to the device 85.

Figure 20:
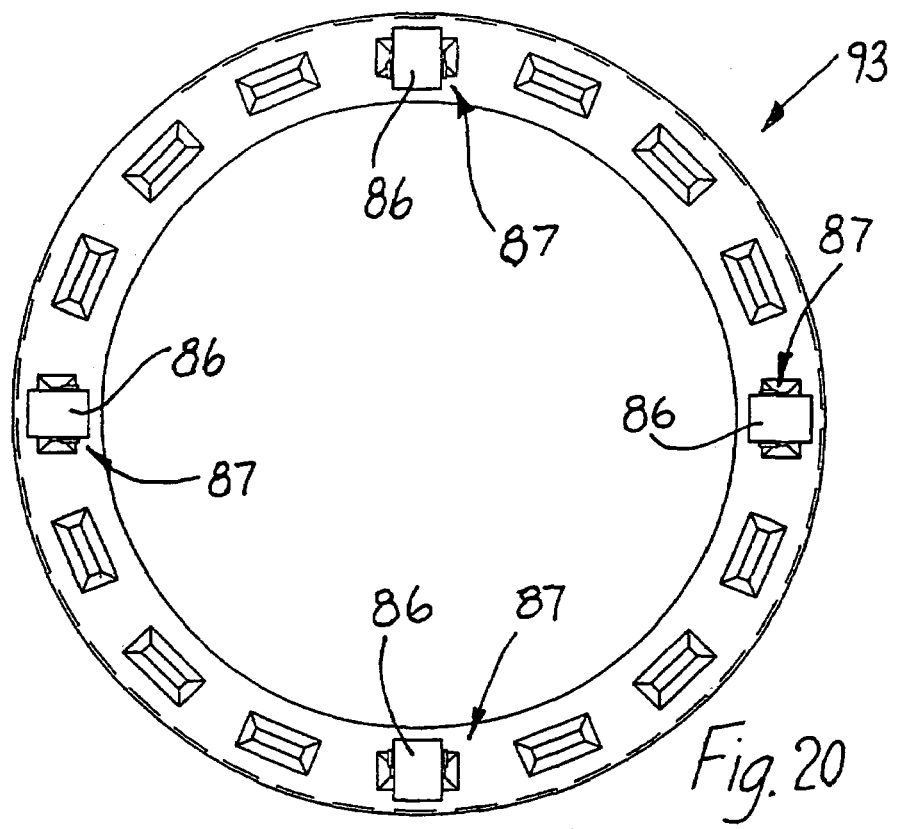
FIG. 20 is a plan view of the device of FIG. 19.
Figure 19:
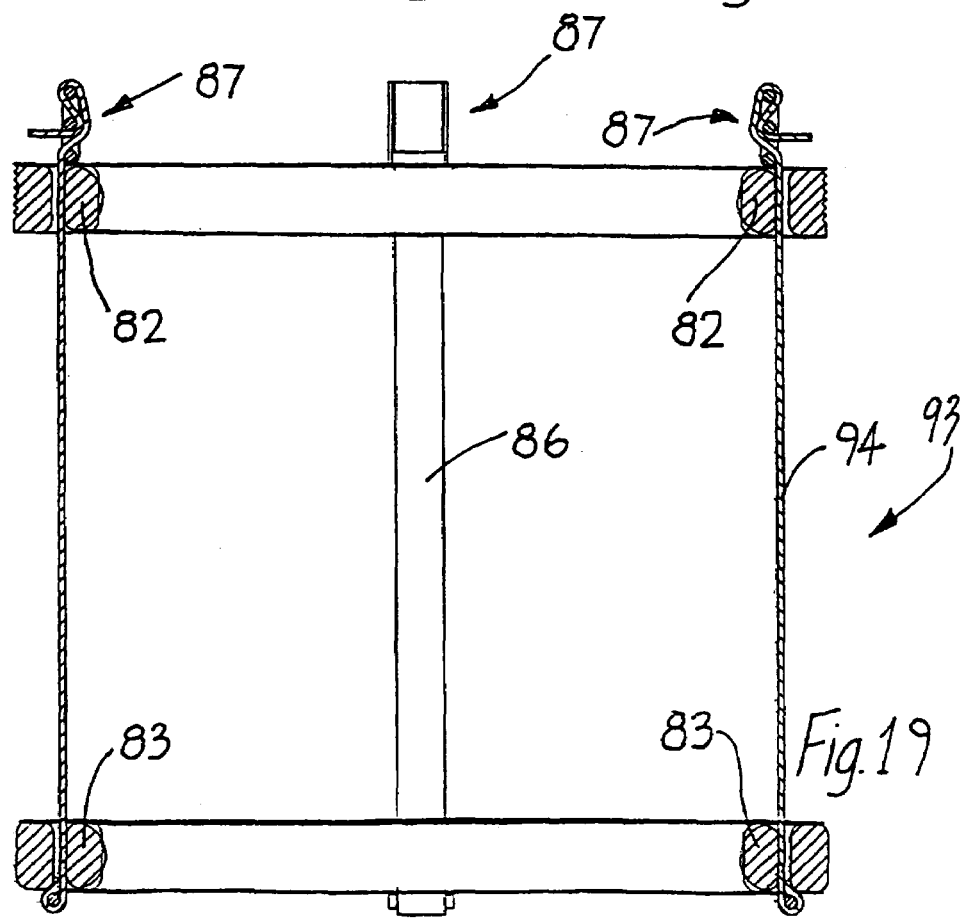
FIG. 19 is a cross sectional view of another surgical device of the invention.

Referring to FIGS. 19 and 20 there is illustrated another surgical device 93 which has single legged straps 94. This device operates in a similar manner to devices 85 and device 90. In this case straps 94 do not loop around the inner ring 83 but are directly attached to it.

Figure 21:
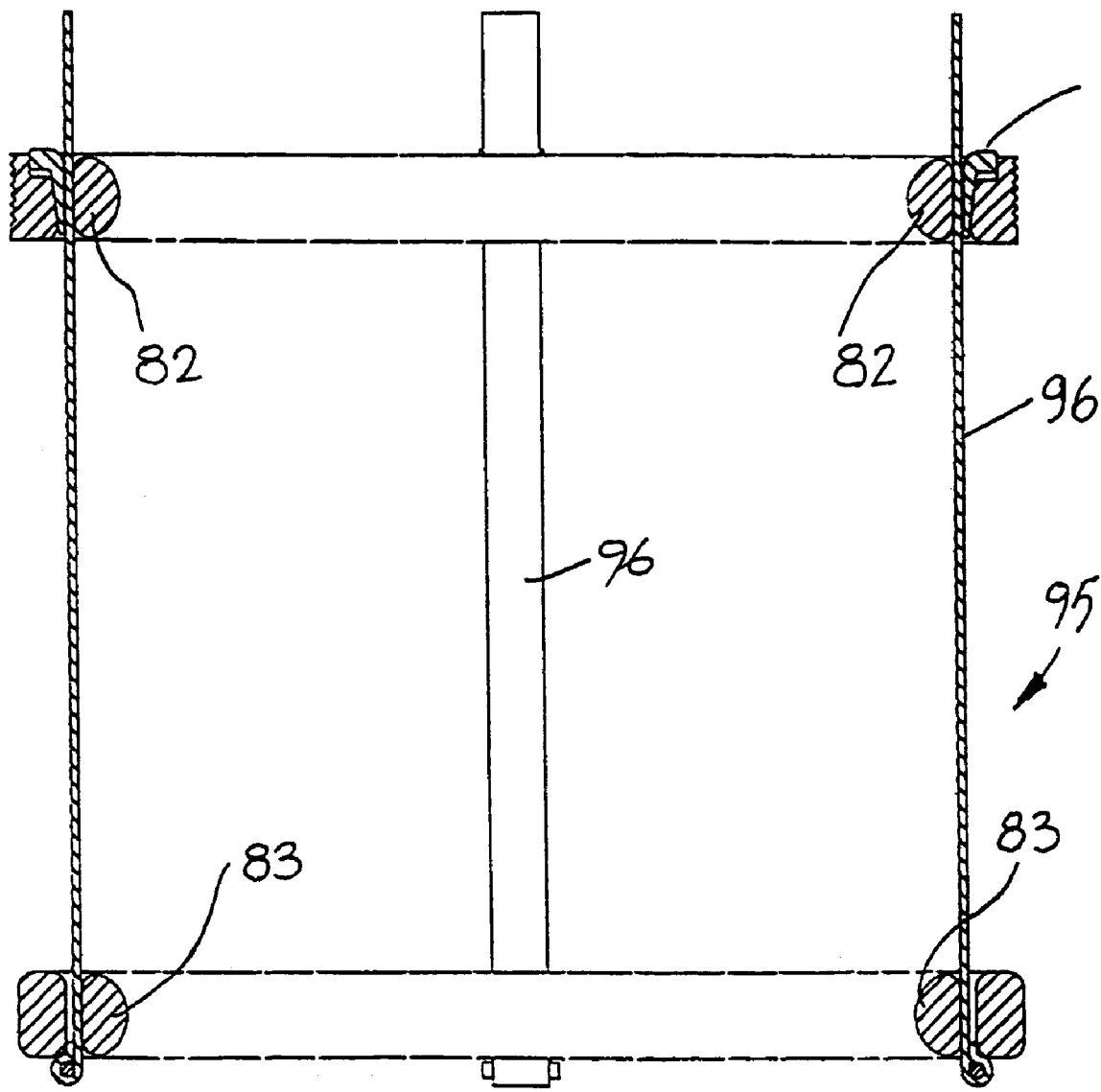
FIG. 21 is a cross sectional view of a further surgical device of the invention.

Referring to FIG. 21 there is illustrated a further surgical device 95 having straps 96 which are locked in position by a locking mechainism. The locking mechanism comprises a wedge 97 inserted into a hole through which the strop 96 passes to hold the strap 96 in position by friction. A ratchet mechanism may also be used or some other adjustable locking mechanism to hold the strap in position.

Figure 23:
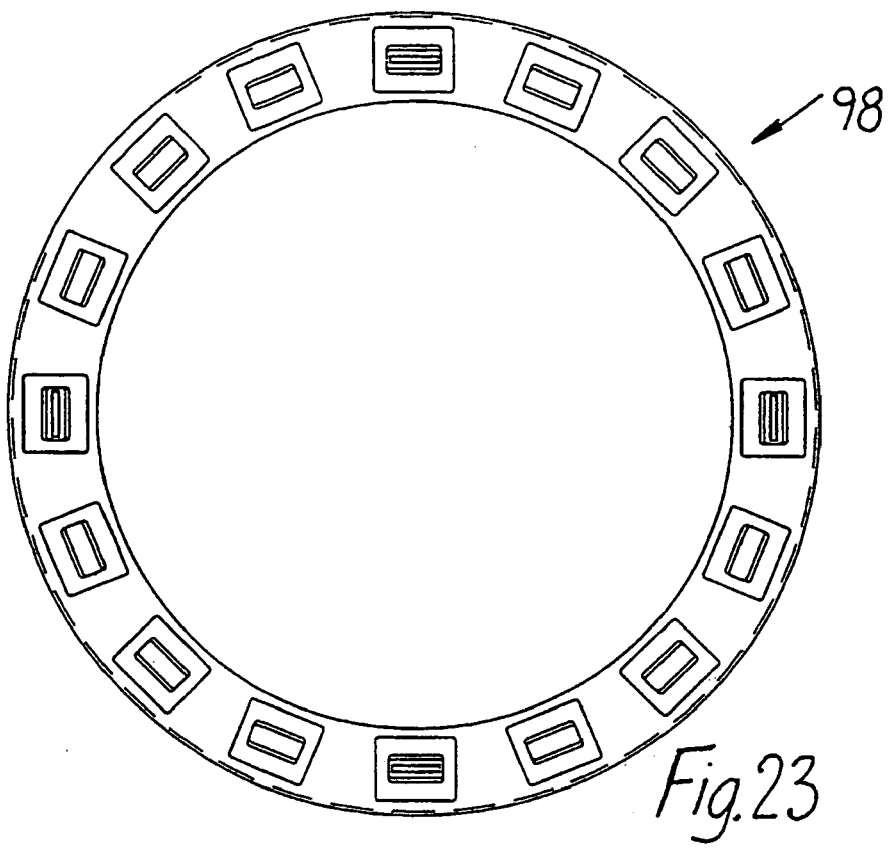
FIG. 23 is plan view of the device of FIG. 22.
Figure 22:
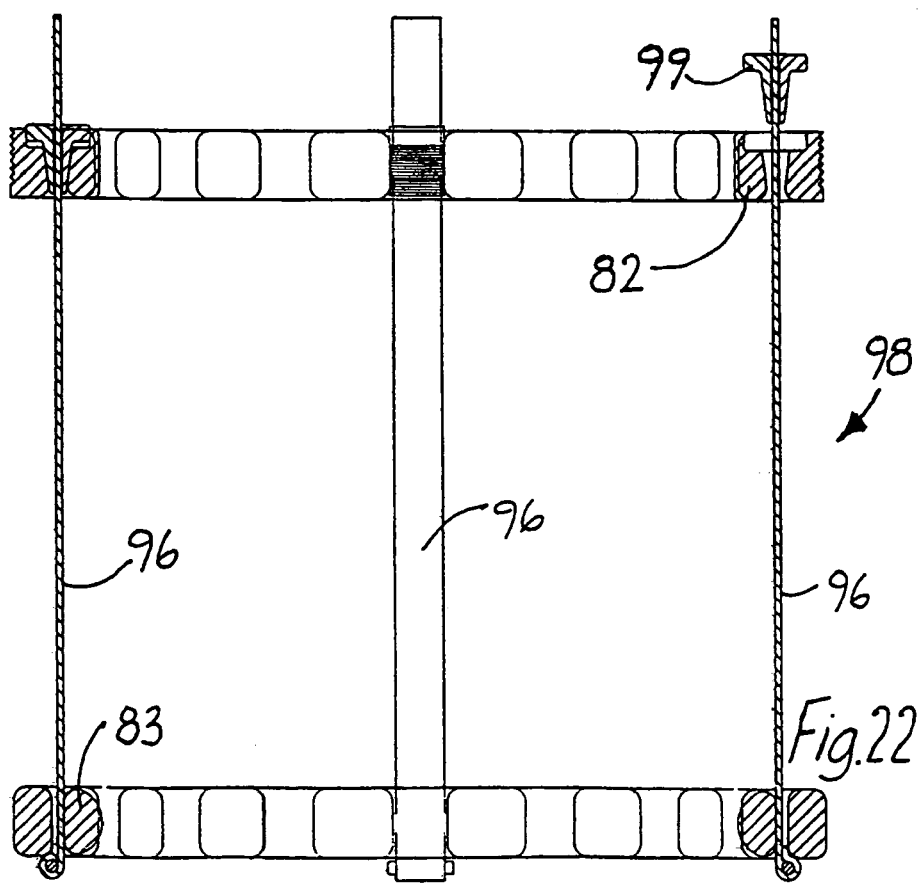
FIG. 22 is a cross sectional view of a still further surgical device of the invention.

The device 98 illustrated in FIGS. 22 and 23 is similar to the device of FIG. 21 except that a different construction of wedge or ratchet 99 is used to lock the straps in position.

Figure 24:
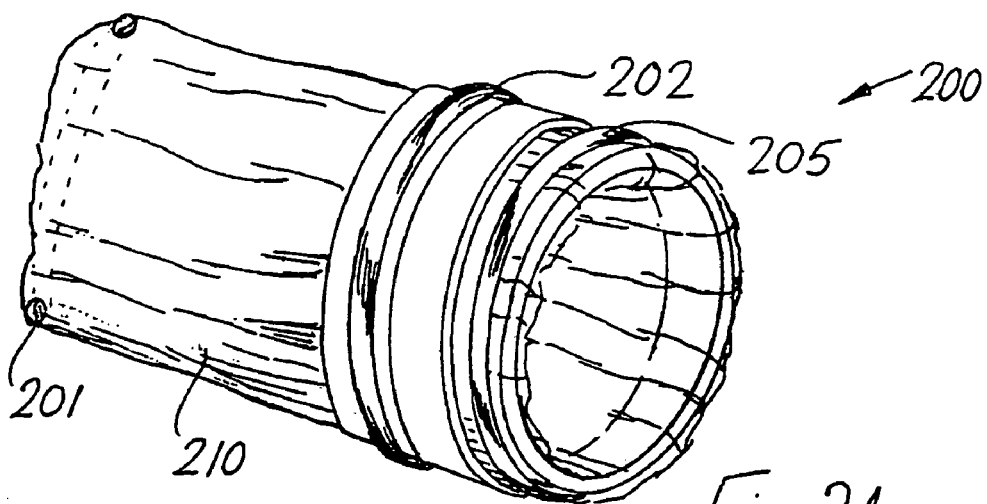
FIG. 24 is a perspective view of another surgical device of the invention.
Figure 25:
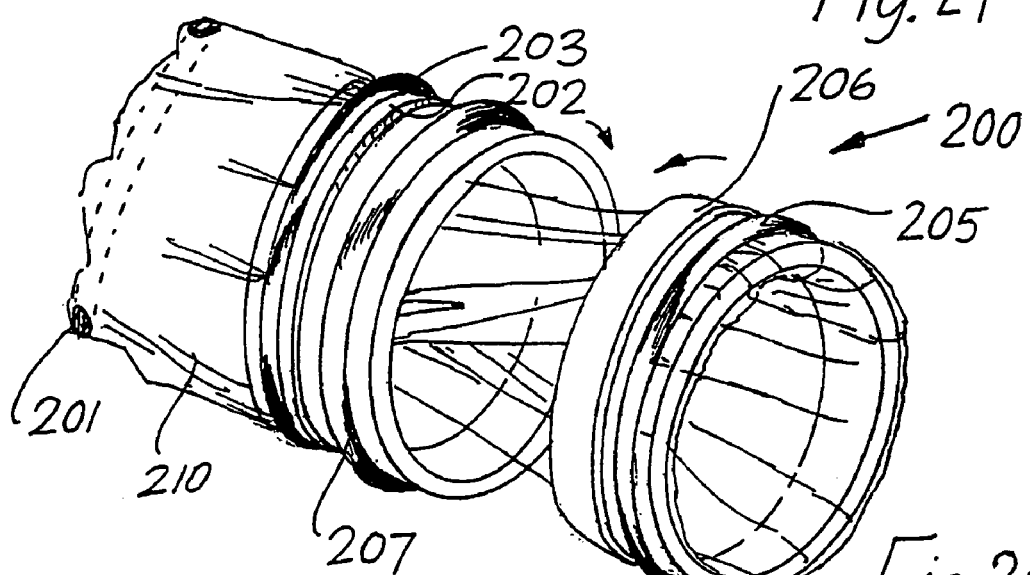
FIG. 25 is a perspective view of the device of FIG. 24 being adjusted.
Figure 26:
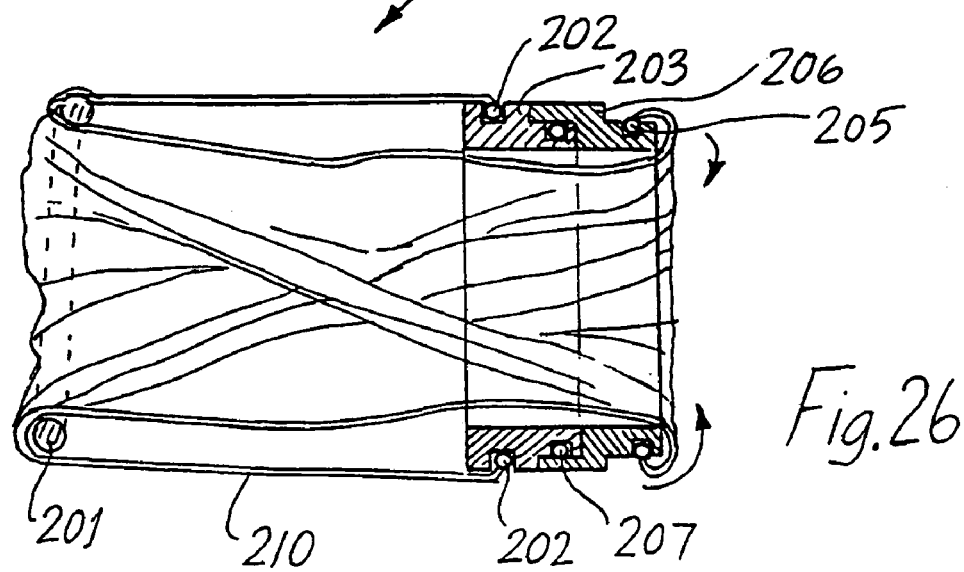
FIG. 26 is a side, partially cross sectional view of the device of FIGS. 24 and 25.

Referring to FIGS. 24 to 26 there is illustrated another surgical device according to the invention. In this case the surgical device is a wound protector retractor 200 of similar construction as that described above with reference to FIGS. 1 to 10. The device 1 comprises an inner mounting means in the form of a first O-ring 201, a first outer mounting means in the form of a second O-ring 202 mounted in a first receiver 203, and a second mounting means in the form of a third O-ring 205 mounted in a second receiver 206. The receivers 203, 206 are in this case interconnectable as illustrated and a fourth O-ring 207 is provided between the receivers 203, 206 on assembly.

A sleeve 210 of flexible pliable plastics material extends from the second outer receiver 206 to the inner O-ring 201 and from the inner O-ring 201 to the first outer receiver 203. The receivers 203, 206 are de-mountable as illustrated in FIG. 25 to facilitate relative rotation therebetween in the direction of the arrows to vary the degree of twist in the sleeve 210.

Figure 27:
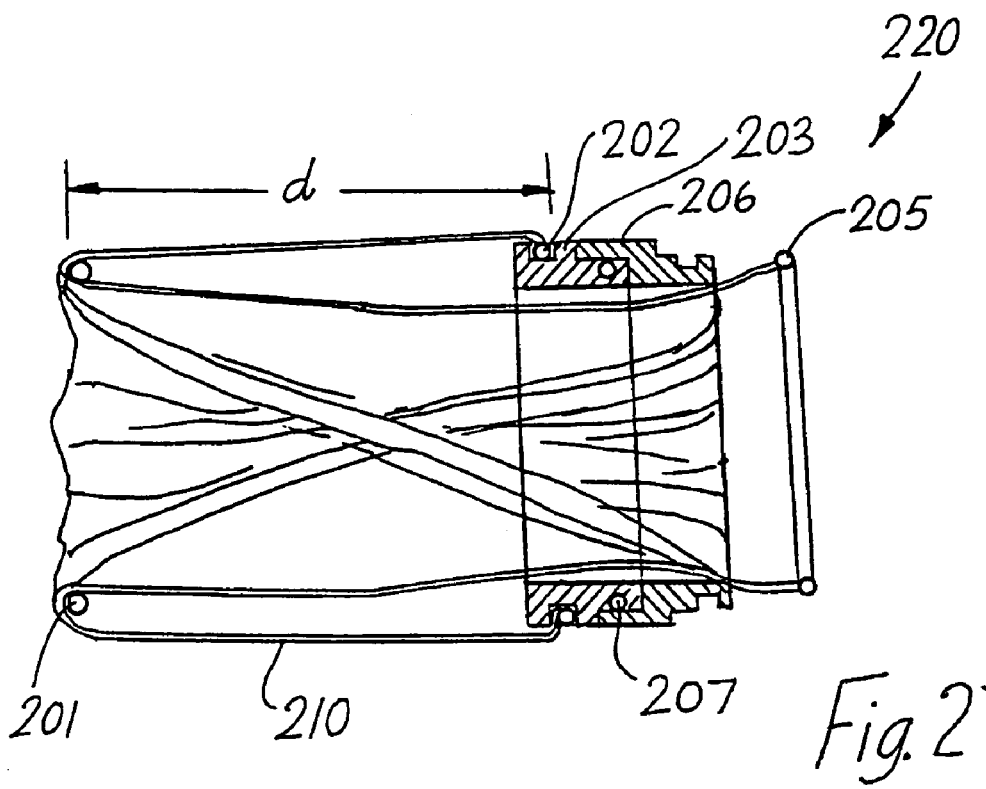
FIG. 27 is a view similar to FIG. 26 of the device partially disassembled.
Figure 28:
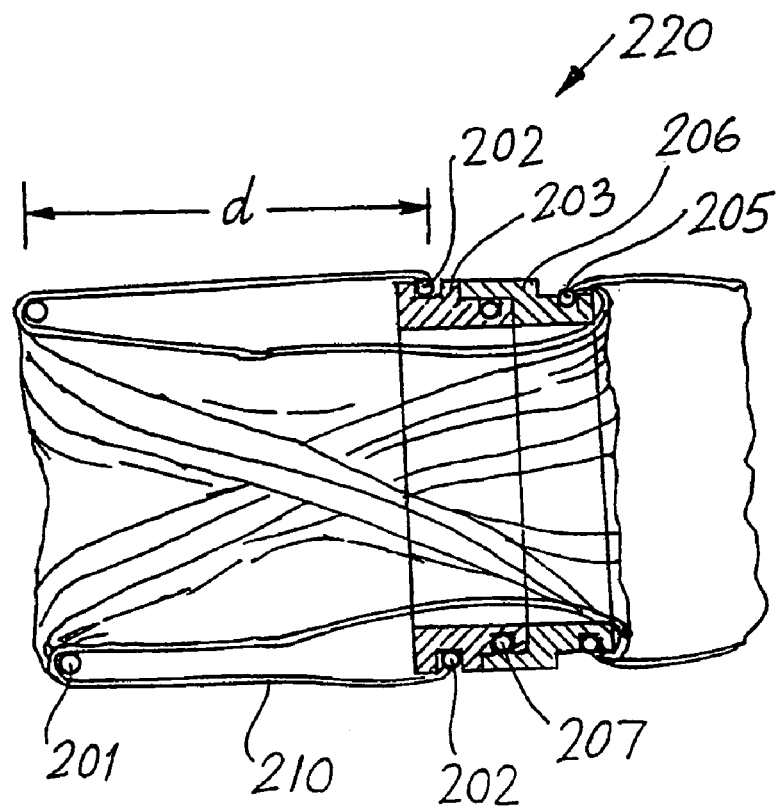
FIG. 28 is a view similar to FIG. 26 with the device of FIG. 27 re-assembled.
Figure 29:
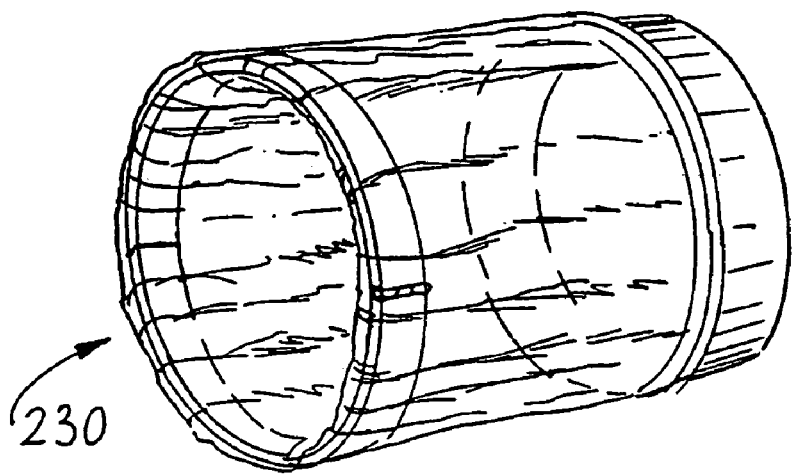
FIG. 29 is a diagrammatic perspective view of another surgical device of the invention.
Figure 30:
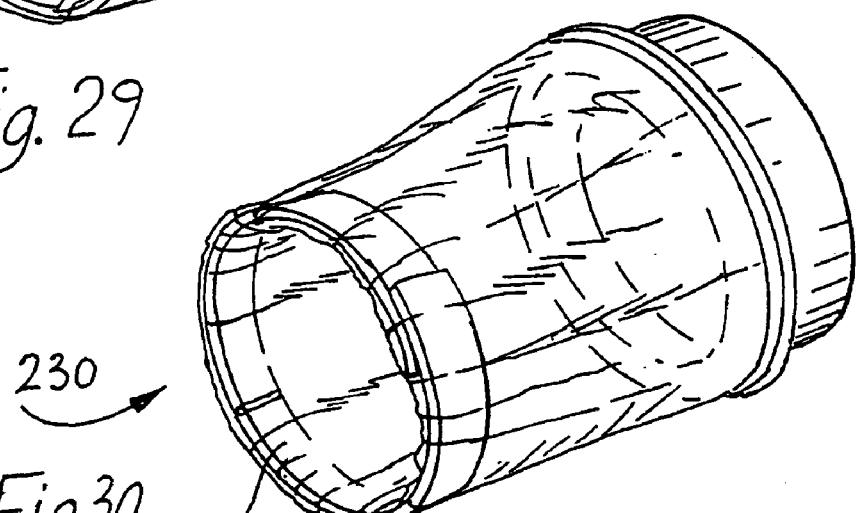
FIG. 30 is a perspective view of the device of FIG. 29 in a wound inserting configuration.
Figure 31:
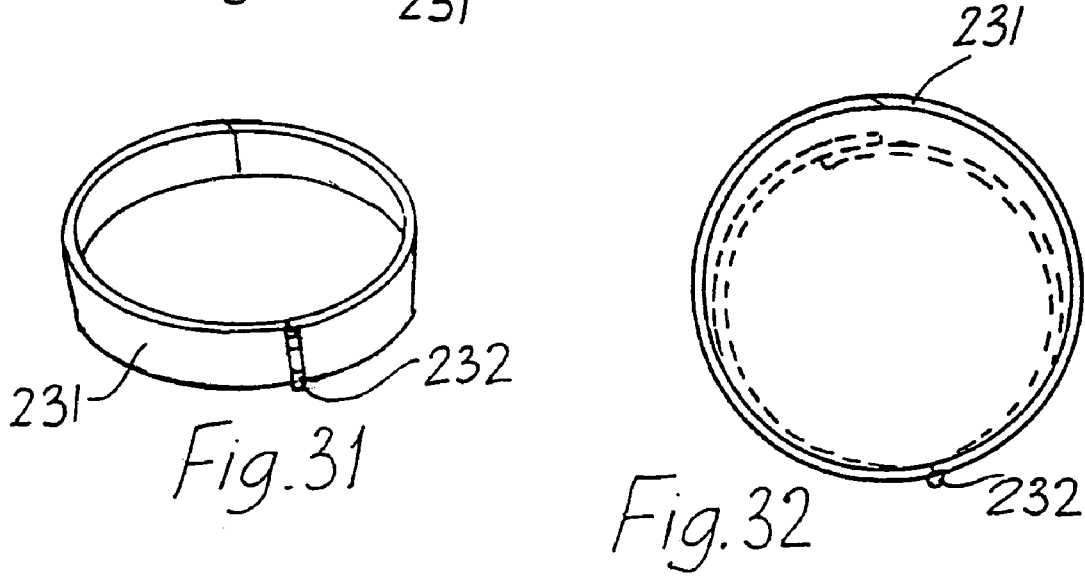
FIGS. 31 and 32 are respectively diagrammatic perspective and plan views of an inner ring part of the device of FIGS. 29 and 30.
Figure 32:
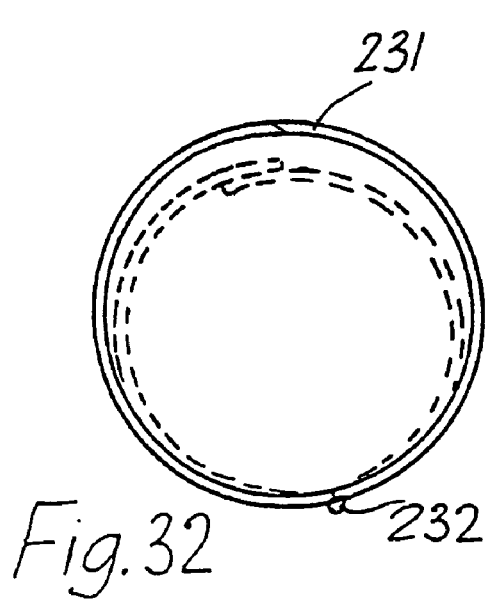

Referring to FIGS. 27 and 28 there is illustrated another surgical device 220 which is similar to the device of FIGS. 24 to 26 and like parts are assigned the same reference numerals. In this case the O-ring 205 is de-mountable from the receiver 206 to facilitate length adjustment of the sleeve 210. On removal of the O-ring 205 the sleeve 210 is adjusted to a desired length d. In this way a single device 220 may be used for a variety of thickness of abdomens. The lumen diameter defined by the twist does not need to be changed to cater for a range of abdomen sizes. The excess sleeve may be cut off or wound around the O-ring seal 205.

Referring now to FIGS. 29 to 32 there is illustrated part 230 of another surgical device according to the invention which is similar to the devices of FIGS. 24 to 28 and like parts are assigned the same reference numerals. An inner mounting means 231 is configured to reduce the size thereof for ease of insertion into a wound opening. In this case the inner mounting means 231 is in the form of a split ring which is hinged at 232 to facilitate a reduction in the diameter of the ring 231 as illustrated. It will of course be appreciated that the hinge may be integrally formed and indeed, there may be a number of such hinges.

Referring to FIGS. 33 and 34 there is illustrated an assembly of two surgical devices 250, 260. The device 250 is a forearm seal and the device 260 is a wound protector retractor which is assembled to an outer sealing device 250. The sealing device 250 provides an outer sealed access port through which a surgeon may insert his forearm or for insertion of an instrument or the like.

Referring to FIGS. 35 to 38 there is illustrated another surgical device 300 according to the invention. The device 300 is a wound protector retractor similar to those described above. In this case the wound protector retractor 300 comprises an inner ring 301 of semi-rigid elastomeric material and an outer ring 302 which is of similar material. A sleeve 303 of pliable material extends between the rings 301, 302. Drawstrings 305 are fitted to the sleeve 303, the drawstrings being pulled outwardly in the direction of the arrows to pull the sleeve 303 upwardly to tighten in the incision and provide a wound protector and retractor.

The invention is not limited to the embodiments hereinbefore described which may be varied in construction and detail.

The invention claimed is:

1. A wound protector and retractor device, comprising:
  a longitudinal axis;
  a distal ring;
  a proximal ring;
  a sleeve extending at least between the distal ring and the proximal ring and proximal to the proximal ring, the sleeve being axially movable relative to the proximal ring to shorten an axial length of the sleeve located between the distal ring and the proximal ring, wherein a portion of the sleeve is slidingly received about a portion of the proximal ring during shortening of the axial length of the sleeve; and
  a securing arrangement configured to substantially fix the axial length of the sleeve located between the distal ring and the proximal ring at a desired length.

2. The wound protector and retractor device of claim 1, wherein the proximal ring forms a part of the securing arrangement.

3. The wound protector and retractor device of claim 1, wherein the sleeve is biased against the proximal ring.

4. The wound protector and retractor device of claim 1, wherein the portion of the proximal ring is a radially outer portion.

5. The wound protector and retractor device of claim 1, wherein the proximal ring is located within the sleeve.

6. The wound protector and retractor device of claim 1, wherein the proximal ring is formed of an elastomeric material.

7. The wound protector and retractor device of claim 1, wherein the distal ring is formed of an elastomeric material.

8. The wound protector and retractor device of claim 1, wherein a portion of the sleeve located between the distal ring and the proximal ring includes two material layers.

9. The wound protector and retractor device of claim 8, wherein the sleeve is wrapped around the distal ring.

10. The wound protector and retractor device of claim 8, wherein an end portion of the sleeve is fixedly secured to the proximal ring.

11. The wound protector and retractor device of claim 1, further including a seal attached to the wound protector and retractor.

12. The wound protector and retractor device of claim 11, wherein the seal includes a forearm seal.

13. The wound protector and retractor device of claim 1, wherein the sleeve has a generally uniform cross-sectional size in a plane normal to the longitudinal axis, the cross-sectional size of the sleeve being substantially equal to a size of at least one of the proximal and distal rings.

14. The wound protector and retractor device of claim 13, wherein the cross-sectional size of the sleeve is substantially equal to a size of both of the proximal and distal rings.

15. The wound protector and retractor device of claim 1, wherein an inner diameter of the proximal ring is substantially equal to an inner diameter of the distal ring.

16. The wound protector and retractor device of claim 1, wherein the proximal ring and distal ring are substantially equal in size.

17. The wound protector and retractor device of claim 1, wherein at least one of the proximal and distal rings includes a substantially circular shape.

18. The wound protector and retractor device of claim 17, wherein both of the proximal and distal rings include a substantially circular shape.

19. The wound protector and retractor device of claim 1, wherein at least one of the proximal and distal rings includes a circular cross-section in a plane containing the longitudinal axis.

20. The wound protector and retractor device of claim 19, wherein both of the proximal and distal rings include a circular cross-section in planes containing the longitudinal axis.

21. A method for retracting an incision comprising:
making an incision in a patient;
providing a wound retractor comprising a central longitudinal axis, a distal ring, a proximal ring, and a sleeve extending at least between the distal ring and the proximal ring, the sleeve being axially movable relative to the proximal ring and proximal to the proximal ring;
inserting the distal ring through the incision such that the sleeve extends through the incision and the proximal ring is located outside of the incision;
sliding a portion of the sleeve against a portion of the proximal ring to shorten an axial length of the sleeve located between the distal ring and the proximal ring; and
securing the sleeve to maintain the shortened axial length of the sleeve located between the distal ring and the proximal ring.

22. A method as claimed in clam 21, wherein the proximal ring is located radially within an end portion of the sleeve.

23. A method as claimed in claim 21, wherein a portion of the sleeve located between the distal ring and the proximal ring includes two material layers.

24. A method as claimed in claim 23, wherein the sleeve is wrapped around the distal ring to form the two material layers.

25. A method as claimed in claim 24, wherein the distal ring is formed of an elastomeric material.

26. A method as claimed in claim 25, wherein an end portion of the sleeve is fixedly secured to the proximal ring.

27. A method as claimed in claim 26, wherein the proximal ring is formed of an elastomeric material.

28. A method as claimed in claim 21, further including sealing the wound retractor.

29. A method as claimed in claim 28, wherein a seal attached to a proximal end of the wound retractor provides said sealing of the wound retractor.

30. A method as claimed in claim 21, wherein the sleeve has a generally uniform cross-sectional size in a plane normal to the longitudinal axis, the cross-sectional size of the sleeve being substantially equal to a size of at least one of the proximal and distal rings.

31. A method as claimed in claim 30, wherein the cross-sectional size of the sleeve is substantially equal to a size of both of the proximal and distal rings.

32. A method as claimed in claim 21, wherein an inner diameter of the proximal ring is substantially equal to an inner diameter of the distal ring.

33. A method as claimed in claim 21, wherein the proximal ring and distal ring are substantially equal in size.

34. A method as claimed in claim 21, wherein at least one of the proximal and distal rings includes a substantially circular shape.

35. A method as claimed in claim 34, wherein both of the proximal and distal rings include a substantially circular shape.

36. A method as claimed in claim 21, wherein at least one of the proximal and distal rings includes a circular cross-section in a plane containing the longitudinal axis.

37. A method as claimed in claim 36, wherein both of the proximal and distal rings include a circular cross-section in planes containing the longitudinal axis.

38. A method as claimed in claim 21, wherein the portion of the proximal ring is a radially outer portion.

* * * * *

UNITED STATES PATENT AND TRADEMARK OFFICE
CERTIFICATE OF CORRECTION

| | |
|---|---|
| PATENT NO. | : 7,300,399 B2 |
| APPLICATION NO. | : 10/995117 |
| DATED | : November 27, 2007 |
| INVENTOR(S) | : Frank Bonadio et al. |

It is certified that error appears in the above-identified patent and that said Letters Patent is hereby corrected as shown below:

In claim 21, column 10, lines 1-2, "proximal ring, the sleeve being axially movable relative to the proximal ring and proximal to the proximal ring" should read --proximal ring and proximal to the proximal ring, the sleeve being axially movable relative to the proximal ring--.

Signed and Sealed this

Second Day of February, 2010

David J. Kappos
*Director of the United States Patent and Trademark Office*